(12) United States Patent
Buzby

(10) Patent No.: US 7,220,549 B2
(45) Date of Patent: May 22, 2007

(54) STABILIZING A NUCLEIC ACID FOR NUCLEIC ACID SEQUENCING

(75) Inventor: Philip Richard Buzby, Brockton, MA (US)

(73) Assignee: Helicos Biosciences Corporation, Cambridge, MA (US)

( * ) Notice: Subject to any disclaimer, the term of this patent is extended or adjusted under 35 U.S.C. 154(b) by 0 days.

(21) Appl. No.: 11/027,165

(22) Filed: Dec. 30, 2004

(65) Prior Publication Data

US 2006/0147942 A1  Jul. 6, 2006

(51) Int. Cl.
*C12Q 1/68* (2006.01)
*C12P 19/34* (2006.01)

(52) U.S. Cl. .......................................... 435/6; 435/91.1
(58) Field of Classification Search ...................... None
See application file for complete search history.

(56) References Cited

U.S. PATENT DOCUMENTS

| | | | |
|---|---|---|---|
| 3,996,345 A | 12/1976 | Ullman et al. |
| 4,119,368 A | 10/1978 | Yamazaki |
| 4,153,855 A | 5/1979 | Feingold |
| 4,344,064 A | 8/1982 | Bitler et al. |
| 4,351,760 A | 9/1982 | Khanna et al. |
| 4,683,195 A | 7/1987 | Mullis et al. |
| 4,683,202 A | 7/1987 | Mullis |
| 4,707,237 A | 11/1987 | Lepp et al. |
| 4,711,955 A | 12/1987 | Ward et al. |
| 4,725,677 A | 2/1988 | Kosler et al. |
| 4,739,044 A | 4/1988 | Slabinsky |
| 4,757,141 A | 7/1988 | Fung et al. |
| 4,793,705 A | 12/1988 | Shera |
| 4,811,218 A | 3/1989 | Hunkapiller et al. |
| 4,863,849 A | 9/1989 | Melamede |
| 4,865,968 A | 9/1989 | Orgel et al. |
| 4,889,818 A | 12/1989 | Gelfand et al. |
| 4,942,124 A | 7/1990 | Church |
| 4,962,037 A | 10/1990 | Jett et al. |
| 4,971,903 A | 11/1990 | Hyman |
| 4,979,824 A | 12/1990 | Mathies et al. |
| 4,994,368 A | 2/1991 | Goodman et al. |
| 4,994,372 A | 2/1991 | Tabor et al. |

(Continued)

FOREIGN PATENT DOCUMENTS

DE           10256898 A1     9/2004

(Continued)

OTHER PUBLICATIONS

Latorra et al., Enhanced allele-specific PCR discrimination in SNP genotyping using 3' locked nucleic acid (LNA) primers. Human Mutation (2003) 22: 79-85.*

(Continued)

*Primary Examiner*—Gary Benzion
*Assistant Examiner*—David C. Thomas
(74) *Attorney, Agent, or Firm*—Thomas C. Meyers; Edwards Angell Palmer & Dodge, LLP

(57) ABSTRACT

The invention provides methods for sequencing a nucleic acid comprising stabilizing a primer/target nucleic acid duplex on a substrate. Methods of the invention generally contemplate the use of a dual-anchored primer/target nucleic acid duplex, or a stabilizing molecule in a single molecule sequencing reaction.

14 Claims, 4 Drawing Sheets

U.S. PATENT DOCUMENTS

| | | |
|---|---|---|
| 4,994,373 A | 2/1991 | Stavrianopoulos et al. |
| 5,085,562 A | 2/1992 | Van Lintel |
| 5,091,652 A | 2/1992 | Mathies et al. |
| 5,096,388 A | 3/1992 | Weinberg |
| 5,096,554 A | 3/1992 | Chin et al. |
| 5,108,892 A | 4/1992 | Burke et al. |
| 5,112,736 A | 5/1992 | Caldwell et al. |
| RE34,069 E | 9/1992 | Koster et al. |
| 5,143,854 A | 9/1992 | Pirrung et al. |
| 5,167,784 A | 12/1992 | Noolandi |
| 5,171,132 A | 12/1992 | Miyazaki et al. |
| 5,198,540 A | 3/1993 | Koster |
| 5,209,834 A | 5/1993 | Shera |
| 5,224,843 A | 7/1993 | Van Lintel |
| 5,242,796 A | 9/1993 | Prober et al. |
| 5,242,797 A | 9/1993 | Hirschfeld |
| 5,258,506 A | 11/1993 | Urdea et al. |
| 5,259,737 A | 11/1993 | Kamisuki et al. |
| 5,260,433 A | 11/1993 | Engelhardt et al. |
| 5,265,327 A | 11/1993 | Faris et al. |
| 5,267,152 A | 11/1993 | Yang et al. |
| 5,302,509 A | 4/1994 | Cheeseman |
| 5,304,487 A | 4/1994 | Wilding et al. |
| 5,306,403 A | 4/1994 | Vo-Dinh |
| 5,336,062 A | 8/1994 | Richter |
| 5,360,523 A | 11/1994 | Middendorf et al. |
| 5,375,979 A | 12/1994 | Trah |
| 5,376,252 A | 12/1994 | Ekstrom et al. |
| 5,403,709 A | 4/1995 | Agrawal et al. |
| 5,405,747 A | 4/1995 | Jett et al. |
| 5,405,783 A | 4/1995 | Pirrung et al. |
| 5,409,811 A | 4/1995 | Tabor et al. |
| 5,424,186 A | 6/1995 | Fodor et al. |
| 5,436,149 A | 7/1995 | Barnes |
| 5,449,767 A | 9/1995 | Ward et al. |
| 5,476,928 A | 12/1995 | Ward et al. |
| 5,484,701 A | 1/1996 | Cocuzza et al. |
| 5,492,806 A | 2/1996 | Drmanac et al. |
| 5,514,256 A | 5/1996 | Douthart et al. |
| 5,518,900 A | 5/1996 | Nikiforov et al. |
| 5,525,464 A | 6/1996 | Drmanac et al. |
| 5,529,465 A | 6/1996 | Zengerle et al. |
| 5,534,125 A | 7/1996 | Middendorf et al. |
| 5,547,839 A | 8/1996 | Dower et al. |
| 5,547,859 A | 8/1996 | Goodman et al. |
| 5,556,790 A | 9/1996 | Pettit |
| 5,558,991 A | 9/1996 | Trainor |
| 5,599,695 A | 2/1997 | Pease et al. |
| 5,610,287 A | 3/1997 | Nikiforov et al. |
| 5,631,734 A | 5/1997 | Stern et al. |
| 5,632,957 A | 5/1997 | Heller et al. |
| 5,654,149 A | 8/1997 | Mendoza et al. |
| 5,659,171 A | 8/1997 | Young et al. |
| 5,670,346 A | 9/1997 | Reeve et al. |
| 5,674,716 A | 10/1997 | Tabor et al. |
| 5,675,155 A | 10/1997 | Pentoney, Jr. et al. |
| 5,688,648 A | 11/1997 | Mathies et al. |
| 5,695,940 A | 12/1997 | Drmanac et al. |
| 5,705,018 A | 1/1998 | Hartley |
| 5,707,506 A | 1/1998 | Douthart et al. |
| 5,710,628 A | 1/1998 | Waterhouse et al. |
| 5,712,476 A | 1/1998 | Renfrew et al. |
| 5,733,729 A | 3/1998 | Lipshutz et al. |
| 5,741,640 A | 4/1998 | FuBer |
| 5,741,644 A | 4/1998 | Kambara et al. |
| 5,744,305 A | 4/1998 | Fodor et al. |
| 5,744,312 A | 4/1998 | Mamone et al. |
| 5,750,341 A | 5/1998 | Macevicz et al. |
| 5,753,788 A | 5/1998 | Fodor et al. |
| 5,755,943 A | 5/1998 | Middendorf et al. |
| 5,756,285 A | 5/1998 | Fuller |
| 5,759,014 A | 6/1998 | Van Lintel |
| 5,759,374 A | 6/1998 | Takahashi et al. |
| 5,762,876 A | 6/1998 | Lincoln et al. |
| 5,763,594 A | 6/1998 | Hiatt et al. |
| 5,776,767 A | 7/1998 | Stevens et al. |
| 5,776,782 A | 7/1998 | Tsuji |
| 5,789,168 A | 8/1998 | Leushner et al. |
| 5,795,722 A | 8/1998 | Lacroix et al. |
| 5,795,782 A | 8/1998 | Church et al. |
| 5,807,679 A | 9/1998 | Kamb |
| 5,808,045 A | 9/1998 | Hiatt et al. |
| 5,830,657 A | 11/1998 | Leushner et al. |
| 5,831,070 A | 11/1998 | Pease et al. |
| 5,832,165 A | 11/1998 | Reichert et al. |
| 5,834,758 A | 11/1998 | Trulson et al. |
| 5,836,750 A | 11/1998 | Cabuz |
| 5,837,832 A | 11/1998 | Chee et al. |
| 5,837,860 A | 11/1998 | Anderson et al. |
| 5,846,396 A | 12/1998 | Zanzucchi et al. |
| 5,846,727 A | 12/1998 | Soper et al. |
| 5,853,979 A | 12/1998 | Green et al. |
| 5,858,671 A | 1/1999 | Jones |
| 5,861,287 A | 1/1999 | Metzker et al. |
| 5,863,722 A | 1/1999 | Brenner |
| 5,872,244 A | 2/1999 | Hiatt et al. |
| 5,876,187 A | 3/1999 | Afomowitz |
| 5,876,934 A | 3/1999 | Duthie et al. |
| 5,882,904 A | 3/1999 | Riedl et al. |
| 5,885,813 A | 3/1999 | Davis et al. |
| 5,889,165 A | 3/1999 | Fodor et al. |
| 5,902,723 A | 5/1999 | Dower et al. |
| 5,908,755 A | 6/1999 | Kumar et al. |
| 5,916,747 A | 6/1999 | Gilchrist et al. |
| 5,922,591 A | 7/1999 | Anderson et al. |
| 5,922,608 A | 7/1999 | Farnsworth et al. |
| 5,928,906 A | 7/1999 | Koster et al. |
| 5,928,919 A | 7/1999 | Reha-Krantz et al. |
| 5,945,283 A | 8/1999 | Kwok et al. |
| 5,945,284 A | 8/1999 | Livak et al. |
| 5,945,312 A | 8/1999 | Goodman et al. |
| 5,945,325 A | 8/1999 | Arnold et al. |
| 5,948,614 A | 9/1999 | Chatterjee |
| 5,952,174 A | 9/1999 | Nikiforov et al. |
| 5,954,932 A | 9/1999 | Takahashi et al. |
| 5,958,703 A | 9/1999 | Dower et al. |
| 5,959,781 A | 9/1999 | Kintz et al. |
| 5,959,837 A | 9/1999 | Yu |
| 5,965,446 A | 10/1999 | Ishikawa |
| 5,968,740 A | 10/1999 | Fodor et al. |
| 5,974,164 A | 10/1999 | Chee |
| 5,976,338 A | 11/1999 | Fujita et al. |
| 5,981,186 A | 11/1999 | Gabe et al. |
| 5,981,956 A | 11/1999 | Stern |
| 5,994,058 A | 11/1999 | Senapathy |
| 5,994,085 A | 11/1999 | Cantor |
| 6,002,471 A | 12/1999 | Quake |
| 6,005,663 A | 12/1999 | Waterhouse et al. |
| 6,007,309 A | 12/1999 | Hartley |
| 6,015,714 A | 1/2000 | Baldarelli et al. |
| 6,017,702 A | 1/2000 | Lee et al. |
| 6,018,041 A | 1/2000 | Drmanac et al. |
| 6,020,457 A | 2/2000 | Klimash et al. |
| 6,024,925 A | 2/2000 | Little et al. |
| 6,025,136 A | 2/2000 | Drmanac |
| 6,028,190 A | 2/2000 | Mathies et al. |
| 6,030,782 A | 2/2000 | Anderson et al. |
| 6,043,080 A | 3/2000 | Lipshutz et al. |
| 6,046,005 A | 4/2000 | Ju et al. |
| 6,049,380 A | 4/2000 | Goodwin et al. |
| 6,051,380 A | 4/2000 | Sosnowski et al. |
| 6,066,454 A | 5/2000 | Lipshutz et al. |
| 6,071,394 A | 6/2000 | Cheng et al. |
| 6,077,664 A | 6/2000 | Slater et al. |

| | | | | | | |
|---|---|---|---|---|---|---|
| 6,077,674 | A | 6/2000 | Schleifer et al. | 6,312,893 B1 | 11/2001 | Van Ness et al. |
| 6,087,095 | A | 7/2000 | Rosenthal et al. | 6,316,191 B1 | 11/2001 | Drmanac et al. |
| 6,087,099 | A | 7/2000 | Gupte et al. | 6,322,968 B1 | 11/2001 | Head et al. |
| 6,094,274 | A | 7/2000 | Yokoi | 6,331,439 B1 | 12/2001 | Cherukuri et al. |
| 6,107,032 | A | 8/2000 | Kilger et al. | 6,333,183 B1 | 12/2001 | Evans et al. |
| 6,107,044 | A | 8/2000 | Nikiforov | 6,335,824 B1 | 1/2002 | Overbeck |
| 6,107,061 | A | 8/2000 | Johnson | 6,337,185 B1 | 1/2002 | Asp et al. |
| 6,132,580 | A | 10/2000 | Mathies et al. | 6,337,188 B1 | 1/2002 | Head et al. |
| 6,133,436 | A | 10/2000 | Koster et al. | 6,342,326 B1 | 1/2002 | Milton |
| 6,136,212 | A | 10/2000 | Mastrangelo et al. | 6,344,325 B1 | 2/2002 | Quake et al. |
| 6,136,962 | A | 10/2000 | Shi et al. | 6,346,379 B1 | 2/2002 | Gelfand et al. |
| 6,140,053 | A | 10/2000 | Koster | 6,346,413 B1 | 2/2002 | Fodor et al. |
| 6,140,494 | A | 10/2000 | Hamilton et al. | 6,355,420 B1 | 3/2002 | Chan |
| 6,141,096 | A | 10/2000 | Stern et al. | 6,355,432 B1 | 3/2002 | Fodor et al. |
| 6,143,151 | A | 11/2000 | Middendorf et al. | 6,361,671 B1 | 3/2002 | Mathies et al. |
| 6,147,205 | A | 11/2000 | McGall et al. | 6,361,937 B1 | 3/2002 | Stryer |
| 6,156,501 | A | 12/2000 | McGall et al. | 6,368,562 B1 | 4/2002 | Yao |
| 6,165,694 | A | 12/2000 | Liu | 6,368,699 B1 | 4/2002 | Gilbert et al. |
| 6,177,249 | B1 | 1/2001 | Kwok et al. | 6,383,749 B2 | 5/2002 | Bochkariov et al. |
| 6,197,506 | B1 | 3/2001 | Fodor et al. | 6,387,626 B1 | 5/2002 | Shi et al. |
| 6,197,595 | B1 | 3/2001 | Anderson et al. | 6,395,232 B1 | 5/2002 | McBride |
| 6,207,381 | B1 | 3/2001 | Larsson et al. | 6,395,559 B1 | 5/2002 | Swenson |
| 6,207,960 | B1 | 3/2001 | Stern | 6,397,150 B1 | 5/2002 | Izmailov |
| 6,210,896 | B1 | 4/2001 | Chan | 6,399,364 B1 | 6/2002 | Reeve et al. |
| 6,214,246 | B1 | 4/2001 | Craighead | 6,401,267 B1 | 6/2002 | Drmanac |
| 6,214,987 | B1 | 4/2001 | Hiatt et al. | 6,403,311 B1 | 6/2002 | Chan |
| 6,221,592 | B1 | 4/2001 | Schwartz et al. | 6,403,315 B1 | 6/2002 | Drmanac |
| 6,221,654 | B1 | 4/2001 | Quake et al. | 6,403,317 B1 | 6/2002 | Anderson |
| 6,225,052 | B1 | 5/2001 | Batz et al. | 6,403,320 B1 | 6/2002 | Read et al. |
| 6,225,062 | B1 | 5/2001 | Dunn et al. | 6,403,957 B1 | 6/2002 | Fodor et al. |
| 6,225,092 | B1 | 5/2001 | Kilger et al. | 6,404,907 B1 | 6/2002 | Gilchrist et al. |
| 6,225,109 | B1 | 5/2001 | Juncosa et al. | 6,406,893 B1 | 6/2002 | Knapp et al. |
| 6,225,567 | B1 | 5/2001 | Kester | 6,407,858 B1 | 6/2002 | Montagu |
| 6,225,625 | B1 | 5/2001 | Pirrung et al. | 6,408,878 B2 | 6/2002 | Unger et al. |
| 6,228,593 | B1 | 5/2001 | Lipshutz et al. | 6,416,952 B1 | 7/2002 | Pirrung et al. |
| 6,232,075 | B1 | 5/2001 | Williams | 6,420,169 B1 | 7/2002 | Read et al. |
| 6,232,103 | B1 | 5/2001 | Short | 6,423,273 B1 | 7/2002 | O'Mara |
| 6,235,465 | B1 | 5/2001 | Kolberg et al. | 6,432,634 B1 | 8/2002 | Digby et al. |
| 6,235,473 | B1 | 5/2001 | Friedman et al. | 6,436,641 B1 | 8/2002 | Izmailov |
| 6,242,180 | B1 | 6/2001 | Chee | 6,436,646 B1 | 8/2002 | Nikiforov |
| 6,242,528 | B1 | 6/2001 | Clark et al. | 6,440,664 B1 | 8/2002 | Digby et al. |
| 6,245,506 | B1 | 6/2001 | Laugharn, Jr. et al. | 6,440,722 B1 | 8/2002 | Knapp et al. |
| 6,245,507 | B1 | 6/2001 | Bogdanov | 6,444,106 B1 | 9/2002 | Mcbride et al. |
| 6,245,518 | B1 | 6/2001 | Baier | 6,444,173 B1 | 9/2002 | Sjursen et al. |
| 6,251,610 | B1 | 6/2001 | Gupte et al. | 6,444,424 B1 | 9/2002 | Chatterjee et al. |
| 6,255,083 | B1 | 7/2001 | Williams | 6,444,461 B1 | 9/2002 | Knapp et al. |
| 6,255,475 | B1 | 7/2001 | Kwiatkowski | 6,447,724 B1 | 9/2002 | Jensen et al. |
| 6,258,533 | B1 | 7/2001 | Jones | 6,448,090 B1 | 9/2002 | McBride |
| 6,261,775 | B1 | 7/2001 | Bastian et al. | 6,451,536 B1 | 9/2002 | Fodor et al. |
| 6,261,776 | B1 | 7/2001 | Pirrung et al. | 6,479,267 B1 | 11/2002 | Davis et al. |
| 6,261,848 | B1 | 7/2001 | Anderson et al. | 6,485,690 B1 | 11/2002 | Pfost et al. |
| 6,262,838 | B1 | 7/2001 | Montagu | 6,485,909 B1 | 11/2002 | Hong et al. |
| 6,263,286 | B1 | 7/2001 | Gilmanshin et al. | 6,485,944 B1 | 11/2002 | Church et al. |
| 6,268,152 | B1 | 7/2001 | Fodor et al. | 6,495,363 B2 | 12/2002 | Bogdanov |
| 6,268,219 | B1 | 7/2001 | Mcbride et al. | 6,506,560 B1 | 1/2003 | Hughes et al. |
| 6,269,846 | B1 | 8/2001 | Overbeck et al. | 6,511,803 B1 | 1/2003 | Church et al. |
| 6,270,644 | B1 | 8/2001 | Mathies et al. | 6,514,706 B1 | 2/2003 | Von Kalle et al. |
| 6,270,961 | B1 | 8/2001 | Drmanac | 6,521,428 B1 | 2/2003 | Senapathy |
| 6,274,320 | B1 | 8/2001 | Rothberg et al. | 6,524,829 B1 | 2/2003 | Seeger |
| 6,274,351 | B1 | 8/2001 | Peponnet | 6,528,258 B1 | 3/2003 | Russell |
| 6,277,604 | B1 | 8/2001 | Peponnet | 6,528,288 B2 | 3/2003 | Senapathy |
| 6,280,954 | B1 | 8/2001 | Ulfendahl | 6,537,755 B1 | 3/2003 | Drmanac |
| 6,284,460 | B1 | 9/2001 | Fodor et al. | 6,537,757 B1 | 3/2003 | Langmore et al. |
| 6,287,821 | B1 | 9/2001 | Shi et al. | 6,546,340 B2 | 4/2003 | Lipshutz et al. |
| 6,294,336 | B1 | 9/2001 | Boyce-Jacino et al. | 6,551,784 B2 | 4/2003 | Fodor et al. |
| 6,294,337 | B1 | 9/2001 | Hayashizaki | 6,551,817 B2 | 4/2003 | Besemer et al. |
| 6,306,607 | B2 | 10/2001 | Williams | 6,554,987 B1 | 4/2003 | Gilchrist et al. |
| 6,309,601 | B1 | 10/2001 | Juncosa et al. | 6,555,349 B1 | 4/2003 | O'Donnell |
| 6,309,701 | B1 | 10/2001 | Barbera-Guillem | 6,558,945 B1 | 5/2003 | Kao |
| 6,309,824 | B1 | 10/2001 | Drmanac | 6,562,566 B1 | 5/2003 | Hoheisel |
| 6,309,836 | B1 | 10/2001 | Kwiatkowski | 6,566,059 B1 | 5/2003 | Stanton, Jr. et al. |
| 6,309,886 | B1 | 10/2001 | Ambrose et al. | 6,566,515 B1 | 5/2003 | McGall et al. |
| 6,310,189 | B1 | 10/2001 | Fodor et al. | 6,573,047 B1 | 6/2003 | Hung et al. |

| | | |
|---|---|---|
| 6,573,374 B1 | 6/2003 | Muehleger et al. |
| 6,576,424 B2 | 6/2003 | Fodor et al. |
| 6,576,425 B2 | 6/2003 | McGall et al. |
| 6,579,704 B2 | 6/2003 | Short |
| 6,582,923 B2 | 6/2003 | Stanton, Jr. et al. |
| 6,585,939 B1 | 7/2003 | Dapprich |
| 6,607,888 B2 | 8/2003 | Schwartz et al. |
| 6,610,482 B1 | 8/2003 | Fodor et al. |
| 6,613,513 B1 | 9/2003 | Parco et al. |
| 6,623,928 B2 | 9/2003 | Van Ness et al. |
| 6,627,748 B1 | 9/2003 | Ju et al. |
| 6,632,655 B1 | 10/2003 | Mehta et al. |
| 6,642,001 B1 | 11/2003 | Bolk et al. |
| 6,664,079 B2 | 12/2003 | Ju et al. |
| 6,719,868 B1 | 4/2004 | Schueller et al. |
| 6,750,018 B2 | 6/2004 | Kambara et al. |
| 6,762,048 B2 | 7/2004 | Williams |
| 6,780,591 B2 | 8/2004 | Williams et al. |
| 6,783,938 B2 | 8/2004 | Nygren et al. |
| 6,787,308 B2 | 9/2004 | Balasubramanian et al. |
| 6,818,395 B1 | 11/2004 | Quake et al. |
| 6,908,736 B1 | 6/2005 | Densham |
| 6,911,345 B2 | 6/2005 | Quake et al. |
| 2001/0024790 A1 | 9/2001 | Kambara et al. |
| 2001/0044531 A1 | 11/2001 | McGall et al. |
| 2001/0046681 A1 | 11/2001 | Senapathy |
| 2002/0009744 A1 | 1/2002 | Bogdanov |
| 2002/0012910 A1 | 1/2002 | Weiss et al. |
| 2002/0015961 A1 | 2/2002 | Kwiatkowski |
| 2002/0025529 A1 | 2/2002 | Quake et al. |
| 2002/0032320 A1 | 3/2002 | Burgess et al. |
| 2002/0034792 A1 | 3/2002 | Kilger et al. |
| 2002/0039738 A1 | 4/2002 | Williams et al. |
| 2002/0042112 A1 | 4/2002 | Koster et al. |
| 2002/0045182 A1 | 4/2002 | Singh et al. |
| 2002/0051992 A1 | 5/2002 | Bridgham et al. |
| 2002/0053532 A1 | 5/2002 | Quake et al. |
| 2002/0061529 A1 | 5/2002 | Bridgham et al. |
| 2002/0072055 A1 | 6/2002 | Jones |
| 2002/0086318 A1 | 7/2002 | Manalis et al. |
| 2002/0102586 A1 | 8/2002 | Ju et al. |
| 2002/0102595 A1 | 8/2002 | Davis |
| 2002/0106673 A1 | 8/2002 | Drmanac et al. |
| 2002/0115076 A1 | 8/2002 | Williams |
| 2002/0115092 A1 | 8/2002 | Rebek, Jr. |
| 2002/0119484 A1 | 8/2002 | Weidenhammer et al. |
| 2002/0123046 A1 | 9/2002 | Smith et al. |
| 2002/0132245 A1* | 9/2002 | Boles et al. ............... 435/6 |
| 2002/0137046 A1 | 9/2002 | Koster |
| 2002/0137052 A1 | 9/2002 | Bridgham et al. |
| 2002/0137062 A1 | 9/2002 | Williams et al. |
| 2002/0138205 A1 | 9/2002 | Miller et al. |
| 2002/0142329 A1 | 10/2002 | Matray et al. |
| 2002/0142333 A1 | 10/2002 | Gelfand et al. |
| 2002/0146704 A1 | 10/2002 | Head et al. |
| 2002/0146726 A1 | 10/2002 | Matray et al. |
| 2002/0150903 A1 | 10/2002 | Koster |
| 2002/0150938 A1 | 10/2002 | Kneipp et al. |
| 2002/0164629 A1 | 11/2002 | Quake et al. |
| 2002/0168642 A1 | 11/2002 | Drukier |
| 2002/0168678 A1 | 11/2002 | Williams et al. |
| 2002/0172948 A1 | 11/2002 | Perlin |
| 2002/0177129 A1 | 11/2002 | Paabo et al. |
| 2002/0182601 A1 | 12/2002 | Sampson et al. |
| 2002/0192661 A1 | 12/2002 | Paabo et al. |
| 2002/0192662 A1 | 12/2002 | Boyce-Jacino et al. |
| 2002/0192691 A1 | 12/2002 | Drmanac |
| 2002/0197618 A1 | 12/2002 | Sampson |
| 2003/0003272 A1 | 1/2003 | Laguitton |
| 2003/0003490 A1* | 1/2003 | Fan et al. ............... 435/6 |
| 2003/0003498 A1 | 1/2003 | Digby et al. |
| 2003/0008285 A1 | 1/2003 | Fischer |
| 2003/0008413 A1 | 1/2003 | Kim et al. |
| 2003/0017461 A1 | 1/2003 | Singh et al. |
| 2003/0022207 A1 | 1/2003 | Balasubramanian et al. |
| 2003/0027140 A1 | 2/2003 | Ju et al. |
| 2003/0036080 A1 | 2/2003 | Jensen et al. |
| 2003/0044778 A1 | 3/2003 | Goelet et al. |
| 2003/0044779 A1 | 3/2003 | Goelet et al. |
| 2003/0044781 A1 | 3/2003 | Korlach et al. |
| 2003/0044816 A1 | 3/2003 | Denison et al. |
| 2003/0054181 A1 | 3/2003 | Swerdlow et al. |
| 2003/0054361 A1 | 3/2003 | Heller |
| 2003/0058440 A1 | 3/2003 | Scott et al. |
| 2003/0058799 A1 | 3/2003 | Yamakawa et al. |
| 2003/0059778 A1 | 3/2003 | Berlin et al. |
| 2003/0060431 A1 | 3/2003 | Simmonds et al. |
| 2003/0064366 A1 | 4/2003 | Hardin et al. |
| 2003/0064398 A1 | 4/2003 | Barnes |
| 2003/0064483 A1 | 4/2003 | Shaw et al. |
| 2003/0087237 A1 | 5/2003 | Hong et al. |
| 2003/0087300 A1 | 5/2003 | Knapp et al. |
| 2003/0092005 A1 | 5/2003 | Levene et al. |
| 2003/0092007 A1 | 5/2003 | Gibbs et al. |
| 2003/0096258 A1 | 5/2003 | Fu et al. |
| 2003/0100006 A1 | 5/2003 | Senapathy |
| 2003/0104437 A1 | 6/2003 | Barnes et al. |
| 2003/0104466 A1 | 6/2003 | Knapp et al. |
| 2003/0108867 A1 | 6/2003 | Chee et al. |
| 2003/0138809 A1 | 7/2003 | Williams et al. |
| 2003/0147344 A1 | 8/2003 | Rothberg et al. |
| 2003/0162213 A1 | 8/2003 | Fuller et al. |
| 2003/0186227 A1 | 10/2003 | Balasubramanian et al. |
| 2003/0186255 A1 | 10/2003 | Williams et al. |
| 2003/0190627 A1 | 10/2003 | Zhao et al. |
| 2003/0190647 A1 | 10/2003 | Odera |
| 2003/0190663 A1 | 10/2003 | Yang et al. |
| 2003/0194722 A1 | 10/2003 | Odedra et al. |
| 2003/0194740 A1 | 10/2003 | Williams |
| 2003/0215862 A1 | 11/2003 | Wallace et al. |
| 2004/0009487 A1 | 1/2004 | Kadushin et al. |
| 2004/0014096 A1 | 1/2004 | Anderson et al. |
| 2004/0029115 A9 | 2/2004 | Dower et al. |
| 2004/0038206 A1 | 2/2004 | Zhang et al. |
| 2004/0054162 A1 | 3/2004 | Hanna |
| 2004/0096853 A1* | 5/2004 | Mayer ............... 435/6 |
| 2004/0106110 A1 | 6/2004 | Balasubramanian et al. |
| 2004/0126770 A1 | 7/2004 | Kumar et al. |
| 2005/0014175 A1 | 1/2005 | Quake et al. |
| 2005/0100932 A1 | 5/2005 | Lapidus et al. |
| 2005/0116262 A1 | 6/2005 | Lapidus |
| 2005/0147992 A1 | 7/2005 | Quake et al. |
| 2005/0170367 A1 | 8/2005 | Quake et al. |
| 2005/0239085 A1 | 10/2005 | Buzby et al. |

FOREIGN PATENT DOCUMENTS

| | | |
|---|---|---|
| EP | 0223618 A2 | 5/1987 |
| EP | 0412883 A1 | 2/1991 |
| EP | 0579997 A1 | 1/1994 |
| EP | 0703364 A1 | 3/1996 |
| EP | 0706004 A2 | 4/1996 |
| EP | 0779436 A2 | 6/1997 |
| EP | 0845603 A1 | 6/1998 |
| EP | 0932700 B1 | 8/1999 |
| EP | 0946752 B1 | 10/1999 |
| EP | 0955085 A2 | 11/1999 |
| EP | 0999055 A2 | 5/2000 |
| EP | 0706004 B1 | 8/2003 |
| GB | 2155152 A | 9/1985 |
| GB | 2308460 A | 6/1997 |
| GB | 2400518 A | 10/2004 |
| SE | 9500589 | 2/1995 |
| WO | 89/03432 A1 | 4/1989 |
| WO | 89/09283 A1 | 10/1989 |
| WO | 90/13666 A1 | 11/1990 |

| | | | | | | |
|---|---|---|---|---|---|---|
| WO | 90/15070 | A1 | 12/1990 | WO | 00/00637 A2 | 1/2000 |
| WO | 91/06678 | A1 | 5/1991 | WO | 00/06770 A1 | 2/2000 |
| WO | 92/10092 | A1 | 6/1992 | WO | 00/09753 A1 | 2/2000 |
| WO | 92/10587 | A1 | 6/1992 | WO | 00/11223 A1 | 3/2000 |
| WO | 93/05183 | A1 | 3/1993 | WO | 00/17397 A1 | 3/2000 |
| WO | 93/06121 | A1 | 4/1993 | WO | 00/26935 A2 | 5/2000 |
| WO | 93/21340 | A1 | 10/1993 | WO | 00/34523 A1 | 6/2000 |
| WO | 95/12608 | A1 | 5/1995 | WO | 00/37680 A1 | 6/2000 |
| WO | 95/27080 | A1 | 10/1995 | WO | 00/40750 A1 | 7/2000 |
| WO | 96/04547 | A1 | 2/1996 | WO | 00/40758 A2 | 7/2000 |
| WO | 96/12014 | A1 | 4/1996 | WO | 00/42223 A1 | 7/2000 |
| WO | 96/12039 | A1 | 4/1996 | WO | 00/43540 A1 | 7/2000 |
| WO | 96/27025 | A1 | 9/1996 | WO | 00/43752 A1 | 7/2000 |
| WO | 97/02488 | A1 | 1/1997 | WO | 00/50642 A1 | 8/2000 |
| WO | 97/22076 | A1 | 6/1997 | WO | 00/53805 A1 | 9/2000 |
| WO | 97/23650 | A2 | 6/1997 | WO | 00/53812 A1 | 9/2000 |
| WO | 97/37041 | A2 | 10/1997 | WO | 00/56937 A2 | 9/2000 |
| WO | 97/39150 | A1 | 10/1997 | WO | 00/58507 A1 | 10/2000 |
| WO | 97/40184 | A1 | 10/1997 | WO | 00/58516 A2 | 10/2000 |
| WO | 97/41258 | A1 | 11/1997 | WO | 00/68410 A1 | 11/2000 |
| WO | 97/41259 | A1 | 11/1997 | WO | 00/70073 A1 | 11/2000 |
| WO | 97/42348 | A1 | 11/1997 | WO | 00/71755 A2 | 11/2000 |
| WO | 98/00708 | A1 | 1/1998 | WO | 00/79007 A1 | 12/2000 |
| WO | 98/02575 | A1 | 1/1998 | WO | 01/001025 A3 | 1/2001 |
| WO | 98/03684 | A1 | 1/1998 | WO | 01/16375 A2 | 3/2001 |
| WO | 98/07069 | A1 | 2/1998 | WO | 01/23610 A2 | 4/2001 |
| WO | 98/13523 | A1 | 4/1998 | WO | 01/24937 A2 | 4/2001 |
| WO | 98/08978 | A1 | 5/1998 | WO | 01/25480 A2 | 4/2001 |
| WO | 98/20019 | A1 | 5/1998 | WO | 01/31055 A2 | 5/2001 |
| WO | 98/20020 | A2 | 5/1998 | WO | 01/32930 A1 | 5/2001 |
| WO | 98/20166 | A2 | 5/1998 | WO | 01/38574 A1 | 5/2001 |
| WO | 98/21361 | A1 | 5/1998 | WO | 01/48184 A2 | 5/2001 |
| WO | 98/27228 | A1 | 6/1998 | WO | 01/42496 A2 | 6/2001 |
| WO | 98/28440 | A1 | 7/1998 | WO | 01/57248 A2 | 8/2001 |
| WO | 98/33939 | A1 | 8/1998 | WO | 01/57249 A1 | 8/2001 |
| WO | 98/40520 | A1 | 9/1998 | WO | 01/61044 A1 | 8/2001 |
| WO | 98/41650 | A2 | 9/1998 | WO | 01/64838 A2 | 9/2001 |
| WO | 98/41657 | A1 | 9/1998 | WO | 01/75154 A2 | 10/2001 |
| WO | 98/44152 | A1 | 10/1998 | WO | 01/79536 A1 | 10/2001 |
| WO | 98/45481 | A1 | 10/1998 | WO | 01/85991 A2 | 11/2001 |
| WO | 98/53300 | A2 | 11/1998 | WO | 01/92284 A1 | 12/2001 |
| WO | 98/54669 | A1 | 12/1998 | WO | 01/96607 A2 | 12/2001 |
| WO | 98/55593 | A1 | 12/1998 | WO | 02/00343 A2 | 1/2002 |
| WO | 99/01768 | A1 | 1/1999 | WO | 02/02584 A2 | 1/2002 |
| WO | 99/05221 | A1 | 2/1999 | WO | 02/02795 A2 | 1/2002 |
| WO | 99/05315 | A2 | 2/1999 | WO | 02/02813 A2 | 1/2002 |
| WO | 99/06422 | A2 | 2/1999 | WO | 02/03305 A2 | 1/2002 |
| WO | 99/13109 | A1 | 3/1999 | WO | 02/04680 A2 | 1/2002 |
| WO | 99/13110 | A1 | 3/1999 | WO | 02/20836 A2 | 3/2002 |
| WO | 99/09616 | A1 | 4/1999 | WO | 02/20837 A2 | 3/2002 |
| WO | 99/17093 | A1 | 4/1999 | WO | 02/27032 A1 | 4/2002 |
| WO | 99/19516 | A1 | 4/1999 | WO | 02/29106 A2 | 4/2002 |
| WO | 99/24797 | A1 | 5/1999 | WO | 02/030486 A3 | 4/2002 |
| WO | 99/27137 | A1 | 6/1999 | WO | 02/35441 A2 | 5/2002 |
| WO | 99/31278 | A1 | 6/1999 | WO | 02/36832 A2 | 5/2002 |
| WO | 99/37810 | A1 | 7/1999 | WO | 02/44414 A2 | 6/2002 |
| WO | 99/39001 | A2 | 8/1999 | WO | 02/061126 A2 | 8/2002 |
| WO | 99/40105 | A2 | 8/1999 | WO | 02/061127 A2 | 8/2002 |
| WO | 99/40223 | A1 | 8/1999 | WO | 02/072779 A2 | 9/2002 |
| WO | 99/41410 | A1 | 8/1999 | WO | 02/072892 A1 | 9/2002 |
| WO | 00/30591 | A1 | 9/1999 | WO | 02/077694 A1 | 10/2002 |
| WO | 99/44045 | A1 | 9/1999 | WO | 02/079519 A1 | 10/2002 |
| WO | 99/45153 | A2 | 9/1999 | WO | 02/088381 A2 | 11/2002 |
| WO | 99/47539 | A1 | 9/1999 | WO | 02/088382 A2 | 11/2002 |
| WO | 99/47706 | A1 | 9/1999 | WO | 02/097113 A2 | 12/2002 |
| WO | 99/53423 | A1 | 10/1999 | WO | 02/099398 A1 | 12/2002 |
| WO | 99/57321 | A1 | 11/1999 | WO | 03/002767 A1 | 1/2003 |
| WO | 99/61888 | A2 | 12/1999 | WO | 03/016565 A2 | 2/2003 |
| WO | 99/64437 | A1 | 12/1999 | WO | 03/021010 A2 | 2/2003 |
| WO | 99/64840 | A1 | 12/1999 | WO | 03/020895 A2 | 3/2003 |
| WO | 99/65938 | A2 | 12/1999 | WO | 03/020968 A2 | 3/2003 |
| WO | 99/66076 | A1 | 12/1999 | WO | 03/031947 A2 | 4/2003 |
| WO | 99/66313 | A1 | 12/1999 | WO | 03/044678 A1 | 5/2003 |

| WO | 03/048178 A2 | 6/2003 |
| WO | 03/048991 A2 | 6/2003 |
| WO | 03/062897 A1 | 7/2003 |
| WO | 03/106642 A2 | 12/2003 |
| WO | 04/061119 A2 | 7/2004 |
| WO | 04/074503 A2 | 9/2004 |
| WO | 05/047523 A2 | 5/2005 |
| WO | 05/080605 A2 | 9/2005 |

OTHER PUBLICATIONS

Takiya et al., Identification of single base-pair mutation on uidA gene of Escherichia coli O157:H7 by peptide nucleic acids (PNA) mediated PCR clamping. Biosci. Biotechnol. Biochem. (2004) 68: 360-368.*
Adam et al., "Individual genomes targeted in sequencing revolution", Nature, vol. 411, p. 402 ( May 2001).
Agrawal, S. et al., "Site Specific Functionalization of Oligodeoxynucleotides for Non-Radioactive Labelling", Tetrahedron Letters, vol. 31, No. 11, pp. 1543-1546 (1990).
Ambrose, W. et al., "Single Molecule Detection With Total Internal Reflection Excitation: Comparing Signal-to-Background and Total Signals in Different Geometries", Cytometry, , vol. 36, pp. 224-231 (1999).
Amit, B. et al., "Photosensitive Protecting Groups of Amino Sugars and Their Use in Glycoside Synthesis . . . Derivatives", 1. Org. Chem., 39(2):192-6 (1974).
Arndt-Jovin, D. et al., "Immunofluorescence Localization of Z-DNA in Chromosomes: Quantitation by Scanning Microphotometry and Computer-assisted Image Analysis", I. The Journal of Cell Biology, vol. 101, pp. 1422-1433, (Oct. 1985).
Augustin, M.A., W. Ankenbauer, and B. Angerer, "Progress towards single-molecule sequencing: enzymatic synthesis of nucleotide-specifically labeled DNA." Journal of Biotechnology, 8(13): 289-301 (2001).
Axelrod, D., "Cell-Substrate Contacts Illuminated by Total Internal Reflection Fluorescenece", 1. The Journal of Cell Biology, vol. 89, pp. 141-145, (Apr. 1981).
Axelrod, D. et al., "Total internal reflection fluorescent microscopy", J Microscopy, vol. 129, pp. 19-28, (1983).
Bai, X., et al., "Photocleavage of a 2-nitrobenzyl linker bridging a fluorophore to the 5' end of DNA" Proc Natl Acad Sci USA, 2003, vol. 100(2). p. 409-13.
Basche, T. et al., "Single Molecule Optical Detection, Imaging and Spectroscopy", Chs. 2 and 3, Weinheim:VCM, Germany (1997).
Beaucage, S. et al., "Advances in the Synthesis of Oligonucleotides by the Phosphoramidite Approach" Tetrahedron, 48:2223-2311 (1992).
Beese, L. et al., "Structure of DNA Polymerase I Klenow Fragment Bound to Duplex DNA", Science, 260:352-355 (1993).
Bennett et al., "Solexa Sequencing chemistry can be applied to different platforms which will have common elements in detection and data processing", Pharamacogenomics 5(4), pp. 433-438, (2004).
Biesalski et al., "Preparation and Characterization of a Polyelectrolyte Monolayer Covalently Attached to a Planar Solid Surface", Macromolecules 111, 32, 2309-2316. Article was published on the web Mar. 10, 1999.
Black, D.L., "Protein diversity from alternating splicing: A challenge for bioinformatics and post genome biology", Cell, 2000. 103(3): p. 367-370.
Blattner, F.R., et al., "The Complete genome sequence of Escherichia coli K-12.", Science, 277: 1453-74 (1997).
Boles et al., "High-Resolution Mapping of Carcinogen Binding Sites on DNA", Biochemistry, 1986, 25, 3039-3043.
Brakmann, S. and P. Nieckchen, "The large fragment of Escherichia coli DNA polymerase I can synthesize DNA exclusively from fluorescently labeled nucleotides," Chembiochem, 2(10): 773-777 (2001).
Brakmann et. al, "Optimal Enzymes for Single-Molecule Sequencing", Current Pharmaceutical Biotechnology, 5, pp. 119-126 (2004).

Braslavsky, I. et al., "Sequence information can be obtained from single DNA molecules", PNAS, vol. 100, No. 7, pp. 3960-3964 (Apr. 2003).
Braslavsky, I. et al., "Objective-type dark-field illumination for scattering from microbeads", Applied Optics, vol. 40, No. 31, pp. 5650-5657, (Nov. 2001).
Braslavsky, I. et al., "Single Molecule Measurements of DNA Polymerase Activity: A Step Towards Single Molecule Sequencing", Biophys. 1. Abstracts, p. 507A (2002).
Brechtel, R. et al., "Control of the electro osmotic flow by metal-salt-containing buffers", J Chromatoraphy A, vol. 716, pp. 97-105, (1995).
Bridgman, A. et al., "An improved method for the synthesis of mercurated dUTP. Enzymatic synthesis of Hg-labelled DNA of high molecular weight suitable for use in an image based DNA sequencing stratgey", DNA Seq., vol. 6, No. 4, pp. 199-209 (1996).
Bruggert, J. et al., "Microfabricated tools for nanoscience", J. Micromech. Microeng., 3, pp. 161-167 (1993).
Bryzek, J. et al., "Micromachines on the march", IEEE Spectrum, vol. 31, No. 5, pp. 20-31, (1994).
Buchaillot, L. et al., "Silicon Nitride Thin Films Young's Modulus Determination by an Optical Non Destructive Method", Jpn. J. Appl. Phys., vol. 36, pp. L794-L797, (Jun. 1997).
Burghardt, T. et al., "Total Internal Reflection Fluorescence Study of Energy Transfer in Surface-Adsorbed and Dissolved Bovine Serum Albumin", Biochemistry, vol. 22, pp. 979-985 (1983).
Burghardt, et al., "Total Internal Reflection/Fluorescence Photobleaching Recovery Study of Serum Albumin Adsorption Dynamics", Biophys. Journal, vol. 33, pp. 455-468 (Mar. 1981).
Butler, D. et al., "Draft data leave geneticists with a mountain still to climb", Nature, vol. 405, Issue 6782, pp. 984-985 (May 2000).
Canard, B., B. Cardona, and R.S. Sarfati, "Catalytic editing properties of DNA polymerases," Proc Natl Acad Sci USA, 92(24): p. 10859-63 (1995).
Canard, et al., "DNA polymerase fluorescent substrates with reversible 3'-tags", Gene, 148(1): 1-6 (1994).
Cheng et al., "High-speed DNA sequence analysis," Prog. in Biochem. and Biophys., vol. 22, pp. 223-227 (1995).
Chicurel, M., "Faster, better, cheaper genotyping", Nature, vol. 412, Issue 6847, pp. 580-582, (Aug. 2001).
Chidgeavadze et al., 2',3'-Dideoxy-3' aminonucleoside 5'-triphosphates are the terminators of DNA synthesis catalyzed by DNA polymerases, Nuc. Acids Res., 12(3):1671-1686 (1984).
Chidgeavadze, Z. et al., "3'-Fluro-2',3'-dideoxyribonucleoside 5'-triphosphates: terminators of DNA synthesis", FEBS Letters, 183(2):275-278 (1985).
Chiu, D. et al., "Patterned deposition of cells and proteins onto surfaces by using three-dimensional microfluidic systems," PNAS, vol. 97, No. 6, pp. 2408-2413 (2000).
Chou et al., "A microfabricated device for sizing and sorting DNA molecules", Applied Sciences, Biophysics: Proc. Natl. Acad. Sci. USA 96, pp. 11-13 (1999).
Chou et al., "A Microfabricated Rotary Pump", Biomedical Microdevices. vol. 3: p. 323-330 (2001).
Close, D. et al., "Ultraviolet Photobleaching of Free Radicals Created in γ-Irradiated Amino Acids", Radiation Research, vol. 53, pp. 349-357 (1973).
Cooper, J. et al., "Analysis of Fluorescence Energy Transfer in Duplex and Branched DNA Molecules", Biochemistry, vol. 29, pp. 9261-9268 (1990).
Crocker, J.C. and D.G. Grier, "Methods of digital video microscopy for colloidal studies." Journal of Colloid and Interface Science, 179(1): p. 298-310 (1996).
Dapprich, J., "Single-molecule DNA digestion by lambda-exonuclease." Cytometry, 36(3): p. 163-168 (1999).
Debenham, J.S., et al., "Two New Orthogonal Amine-Protecting Groups that can be Cleaved under Mild or Neutral Conditions." Journal of the American Chemical Society, 117(11): p. 3302-3 (1995).
Decher, G. et al. "Buildup of ultrathin multiplayer films by a self-assembly process: III. Consecutively alternating absorption of anionic and cationic polyelectrolytes on charged surfaces", Thin Solid Films, 210:831-835 (1992).

Decher G.; et al., "Fuzzy nanoassemblies : Toward layered polymeric multicomposites." *Science*, 277(5330): p. 1232-1237 (1997).

Delamarche, E. et al., "Patterned Delivery of Immunoglobulins to Surfaces Using Microfluidic Networks", *Science* 276:779-781 (1997).

Dickson et al., "Simultaneous Imaging of Individual Molecules aligned both parallel and perpendicular to the optic axis", *The American Physical Society*, vol. 81, No. 24, pp. 5322-5325 (1998).

Doktycz, M. et al., "Genosensors and Model Hybridization Studies", *Automation Technologies for Genome Characterization*, Ch. 10 T. Beugelsdijk (Ed), John Wiley & Sons, Inc., pp. 205-225 (1997).

Doublie, S. et al., "Crystal structure of a bacteriophage T7 DNA replication complex at 2.2 A resolution", *Nature*, vol. 391, pp. 251-258 (Jan. 1998).

Driscoll et al., "Atomic-Scale Imaging of DNA Using Scanning Tunneling Microscopy." *Nature*, 346(6281): p. 294-296 (1990).

Drmanac, R. et al., "Sequencing by hybridization: Towards an automated sequencing of one million M13 clones arrayed membranes", *Electrophoresis*, 13:566-573 (1992).

Duffy et al., "Patterning Electroluminescence Materials with Feature Sizes as Small as 5 um Using Elastomeric Membrains as Marks for Dry Lift-Off," *Advanced Materials* vol. 11, No. 7, pp. 546-552 (1999).

Duffy et al., "Rapid prototyping of microfluidic switches in poly(dimethyl siloxane) and their acuation by electroosmotic flow," *J. Micromech. Microeng.*, vol. 9, pp. 211-217 (1999).

Duffy et al., "Rapid Prototyping of Microfluidic Systems in Poly(dimethylsiloxane)", *Analytical Chemistry*, vol. 70, No. 23, pp. 4974-4984 (1998).

Effenhauser et al., "Integrated capillary electrophoresis on Flexible silicone microdevices: Analysis of DNA restriction fragments and detection of single DNA molecules on microchips," *Anal. Chem.*, vol. 69, pp. 3451-3457 (1997).

Effenhauser et al., "Integrated chip-based capillary electrophoresis," *Electrophoresis*, vol. 18, pp. 2203-2213 (1997).

Elgen, M. et al., "Sorting single molecules: Application to diagnostics and evolutionary biotechnology", *PNAS*, vol. 91, pp. 5740-5747, (Jun. 1994).

Evangelista, R.A., et al. "Characterization of fluorescent nucleoside triphosphates by capillary electrophoresis with laser-induced fluorescence detection: action of alkaline phosphatase and DNA polymerase." *Analytical Biochemistry*, 235(1): p. 89-97 (1996).

Fahrenberg et al., "A microvalve system fabricated by thermoplastic molding," *J. Micromech. Microeng.*, vol. 5, pp. 169-171 (1995).

Ferguson, et al., "A fiber-optic DNA biosensor microarray for the analysis of gene expression," *Nature Biotechnology*, vol. 14, pp. 1681-1684 (1996).

Forster, T., "Delocalized Excitation and Excitation Transfer", *Modern Quantum Chem., Istanbul Lectures*, Part TII, pp. 93-137, Academic Press, New York (1965).

Fritz, I. et al., "Electronic detection of DNA by its intrinsic molecular charge", *PNAS*, vol. 99, No. 22, pp. 14142-14146 (Oct. 2002).

Fu et al., "A microfabricated fluorescence-activated cell sorter," *Nature Biotechnology*, vol. 17, pp. 1109-1111 (1999).

Fu e al., "An integrated microfabricated cell sorter", *Analytical Chemistry*, 74(11): pp. 2451-2457 (2002).

Funatsu, T. et al., "Imaging of single fluorescent molecules and individual ATP turnovers by single myosin molecules in aqueous solution", *Nature*, vol. 374, pp. 555-559 (Apr. 1995).

Garcia, A., "Determination of Ion Penneability by Fluorescence Quenching", *Meth. in Enzymology*, 207:501-511 (1992).

Gardner, A., et al. "Acyclic and dideoxy terminator preferences denote divergent sugar recognition by archaeon and *Taq* DNA polymerases", *Nucleic Acids Research*, vol. 30, No. 2, pp. 605-613 (2002).

Gardner et al., "Comparative kinetics of nucleotide analog incorporation by Vent DNA polymerase," *J. Biol. Chem.*, 279, No. 12, p. 11834-11842 (2004).

Giller et al., "Incorporation of reporter molecule-labeled nucleotides by DNA polymerases. 1. Chemical synthesis of various reporter group-labeled 2'deoxyribonucleoside-5'-triphosphates," *Nucleic Acids Res.*, 31, No. 10, p. 2630-2635 (2003).

Giusti, W. et al., "Synthesis and Characterization of 5'-Fluorescent-dye-labeled Oligonucleotides", *PCR Methods and Applications*, 2:223-227 (1993).

Goll et al., "Microvalves with bistable buckled polymer diaphragms," *J. Micromech. Microeng.*, vol. 6., pp. 77-79 (1996).

Goodwin, P.M., et al., "Application of single molecule detection to DNA sequencing." *Nucleosides & Nucleotides*, 16(5-6): p. 543-550 (1997).

Gravesen et al., "Microfluidics—a review", *J. Micromech. Microeng.*, vol. 3, pp. 168-182 (1993).

Greene, T.W. and P.G.M. Wuts, "Protective Groups in Organic Synthesis." John Wiley and Sons, Inc.: New York, 1999 3rd Ed.

Gueroui, Z., et al., "Observation by fluorescence microscopy of transcription on single combed DNA," *PNAS*, 99(9): p. 6005-6010 (2002).

Guilbault, G., "Practical Fluorescence—Theory, Methods and Techniques," Chapters 1 and 3, and pp. 521-524, Marcel Dekker, Inc., New York (1973).

Guillier, F., D. Orain, and M. Bradley, "Linkers and Cleavage Strategies in Solid-Phase Organic Synthesis and Combinatorial Chemistry." Chemical Reviews, 100(6): p. 2091-2157 (2000).

Gupta, K.C., et al., "A general method for the synthesis of 3'-sulfhydryl and phosphate group containg oligonucleotides", *Nucleic Acids Res.*, 1901:3019-25 (1991).

Gyllenstein, U. et al., "Generation of single-stranded DNA by the polymerase chain reaction and its application to direct sequencing of the *HLA-DQA* locus", *PNAS*, 85:7652-56 (1988).

Ha, "Single molecule dynamics studied by polarization modulation," *Phys. Rev. Lett.*, 77, No. 19, 3979-3982 (1996).

Ha, "Single molecule spectroscopy with automated positioning," *Appl. Phys. Lett.* 70, No. 6, 782-784 (1997).

Ha, "Single-molecule fluorescence methods for the study of nucleic acids," Current Opinion in Structs Bio, 11, 287-292 (2001).

Ha, "Single-molecule fluorescence spectroscopy of enzyme conformational dynamics and cleavage mechanism," *PNAS*, 96(3): p. 893-898 (1999).

Ha, T., "Single-molecue fluorescence resonance energy transfer," *Methods*, 25(1): p. 78-86 (2001).

Hanna, M. et al., "Synthesis and characterization of a new photocrosslinking CTP analog and its use in photoaffmity labeling *E. coli* and T7 RNA polymerases", *Nucleic Acids Res.*, 21(9):2073-2079 (1993).

Hansen, C.J., et al., "A robust and scalable microfluidic metering method that allows Protein crystal growth by free interface diffusion". Proc Natl Acad Sci U S A, 99 (26): p. 16531-6 (2002).

Harding et al., "Single-molecule detection as an approach to rapid DNA sequencing," Trends in Biotechnology, vol. 10, 3 pages, (1992).

Harris, J.M., "Introduction to Biochemical and biomedical appliations of poly(ethylene glycol)." Poly(ethylene glycol) Chemistry, Harris, J. M., Ed.; Plenum Press: New York, pp. 1-14 (1992).

Harrison et al., "Micromachining a miniaturized capillary electrophoresis-based chemical analysis system on a chip," Science, vol. 261, pp. 895-897 (1993).

Harrison, D., et al., "Towards miniaturized electrophoresis and chemical analysis systems on silicon: an alternative to chemical sensors", *Sensors and Actuators B*, 10, pp. 107-116 (1993).

Hasan, A. et al., "Photoabile Protecting Groups for Nucleosides: Synthesis and Photodeprotection Rates", *Tetrahedron*, 53(12):4247-4264 (1997).

Hornbeck, L. et al., "Bistable Defonnable Mirror Device", 1988 Techllical Digest Series, vol. 8, Optical Society of America, pp. 107-110, (Jul. 1988).

Hosokawa et al., "Handling of Picoliter liquid samples in a poly(dimethylsiloxane)-based microfluidic device," *Anal. Chem.*, vol. 71, No. 20, pp. 4781-4785 (1999).

Houseal, T. et al., "Real-time imaging of single DNA molecules with fluorescence microscopy", *Biophys. I.*, vol. 56, pp. 507-516 (Sep. 1989).

Howorka, et al., "Sequence-specific detection of individual DNA strands using engineered nanopores." Nature Biotechnology, 19(7): p. 636-639 (2001).

Hubner et al., "Direct oberservation of the triplet lifetime quenching of single dye molecules by molecular oxygen," J. Chem. Physics, 115, No. 21, p. 9619-9622 (2001).

Hultman, T. et al., "Bidirectional Solid-Phase Sequencing of In Vitro-Amplified Plasmid DNA", BioTechniques, vol. 10, No. 1, pp. 84-93 (1991).

Hyman, E., "A New Method of Sequencing DNA", Anal. Biochem., 174:423-436 (1988).

Ikuta et al., "Three dimensional micro integrated fluid systems (MIFS) fabricated by stereo lithography", IEEE Kyushu Institute of Technology, pp. 1-6, (1994).

Ishii et al., "Fluorescence resonance energy transfer between single fluorophores attached to a coiled-coil protein in aqueous solution," Chemical Physics, 247, 163-173 (1999).

Ishijima, A. et al., "Simultaneous Observation of Individual ATPase and Mechanical Events by a Single Myosin Molecule during Interaction with Actin", Cell, vol. 92, pp. 161-171, (Jan. 1998).

Ishikawa, M. et al., "Single-Molecule Detection by Laser-Induced Fluorescence Technique with a Position-Sensitive Photon-Counting Apparatus", Appl. Phys., vol. 33, Part 1, No. 3A, pp. 1571-1576 (1994).

Jacobs et al., "Combinatorial chemistry—applications of light-directed chemical synthesis", TIBTech, vol. 12, pp. 19-26 (Jan. 1994).

Jacobson, K. et al., "International Workshop on the application of fluorescence photobleaching techniques to problems in cell biology", Workshop Summary, Federation Proceedings, vol. 42, pp. 72-79 (1983).

Jacobson, et al., "High-speed separations on a microchip," Anal. Chem., vol. 66, No. 7, pp. 1114-1118 (1994).

Jacobson, et al., Microfluidic devices for electrokinetically driven parallel and serial mixing, Anal. Chem., vol. 71, No. 20, pp. 4455-4459 (1999).

Jett, J. et al., "High-Speed DNA Sequencing: An Approach Based Upon Fluorescence Detection of Single Molecules", J. Biomolecular Structure & Dynamics, vol. 7, No. 2, pp. 301-309, (1989).

Johnston, R. et al., "Autoradiography using storage phosphor technology", Electrophoresis, 11 :355-360 (1990).

Jongeneel, C.V., et al., "Comprehensive sampling of gene expression human cell lines with massively parallel signature sequencing", Proc Natl Acad Sci U S A, 100(8): p. 636-639 (2003).

Joos, B. et al., "Covalent Attachment of Hybridizable Oligonucleotides to Glass Supports", Anal. Biochem. 247(1):96-101 (1997).

Kambara, H. et al., "Optimization of Parameters in a DNA Sequenator using Fluorescence Detection", Biotechnology, vol. 6, pp. 816-821 (1988).

Kartalov, Emil P., et al., "Microfluidic device reads up to four consecutive base pairs in DNA sequencing-by-synthesis", Nucleic Acids Research, vol. 32, No. 9, pp. 2873-2879 (2004).

Kartalov et al., "Single-Molecule Detection and DNA Sequencing-by-Synthesis," In Partial Fulfillment of the Requirements for the Degree of Doctor Philosophy, California Institute of technology, pp. 1-160 (2004).

Kartalov et al., Poly-Electrolyte Surface-Chemistry Platform for Fluorescence Studies of DNA on Glass http://www.ugcs.caltech.edu/~kartalov/PEM_6.pdf, pp. 1-7, last modified Jun. 7, 2002.

Kawai et al., "A simple method of detecting amplified DNA with immobilized probes on microtiter wells", Analytical Biochemistry, 209:63-69 (1996).

Kelso et al., "Single-cell analysis by RT-PCR reveals differential expression of multiple type 1 and 2 cytokine genes among cells within polarized CD4+ T cell populations," International Immunology, 11, No. 4, 617-621 (1999).

Kenis et al., "Microfabrication inside capillaries using multiphase laminar flow patterning," Science, vol. 285, pp. 83-85 (1999).

Kenney, et al., "Mutation Typing Using Electrophoresis and Gel-Immobilized Acrydite™ Probes," BioTechniques, vol. 25, No. 3, pp. 516-521, (1998).

Khandjian, E., "UV cross linking of RNA to nylon membrane enhances hybridization signals", Mole. Bio, Rep. 11: 107-115 (1986).

Khrapko, K. et al., "A method for DNA sequencing by hybridization with oligonucleotide matrix", DNA Seequence-J. DNA Sequencing and Mapping, vol. 1, pp. 375-388 (1991).

Kiefer, J. et al., "Crystal structure of thermostable Bacillus DNA polymerase I large fragment at 2.1 A resolution", Structure, 5:95-108 (1997).

Kim, Y. et al., "Crystal structure of Thermus aquaticus DNA polymerase", Nature, 376:612-616 (1995).

Kirkland, T.A., D.M. Lynn, and R.H. Grubbs, "Ring-Closing Metathesis in Methanol and Water." Journal of Organic Chemistry, 63(26): p. 9904-9909 (1998).

Knerr, L. and R.R. Schmidt, "Application of a ring-closing-metathesis-based linker to the solid phase synthesis of oligosaccharides" Synlett, 11: p. 1802-1804 (1999).

Kopp, et al., "Chemical Amplification: Continuous-Flow PCR on a Chip", Science, vol. 280, pp. 1046-1048 (May 1998).

Korolev, S. et al., "Crystal structure of the large fragement of Thermus aquaticus DNA polymerase I at 2.5 A resolution: Structural basis for thermo stability", PNAS, 92:9264-9268 (1995).

Kovacs et al., "Simple synthesis of 5-vinyl-and 5-ethynyl-2' deoxyuridine 5'-triphosphates", Tetrahedron Letters, 29(36): p. 4525-8 (1988).

Kricka et al., "Labels, Labeling, Analytical Strategies, and Applications." Ch 1 and Table Ix, Academic Press, New York, pp. 3-40, (1995).

Krider, E. et al., "2'-Modified Nucleosides for Site-Specific Labeling of Oligonucleotides", Bioconjugate Chem., vol. 13, No. 1, pp. 155-162 (2002).

Kuhn, L. et al., "Silicon Charge Electrode Array for Ink Jet Printing", IEEE Trans. On Electron Dev., vol. ED-25, No. 10, pp. 1257-1260 (Oct. 1978).

Lacoste, T. et al., "Ultrahigh-resolution multicolor colocalization of single fluorescent probes", PNAS, 97(17):9461-6 (2000).

Lander, E.S., et al., "Initial sequencing and analysis of the human genome." Nature, 409(6822): p. 860-921 (2001).

Lazowski, K. et al., "Highly Sensitive Detection of Hybridization of Oligonucleotides to Specific Sequences of Nucleic Acids by Application of Fluorescence Resonance Energy Transfer", Antisense and Nucleic Acid Drug Dev., vol. 10, pp. 97-103 (2000).

Lee, "Enhancing the catalytic repertoire of nucleic acids: a systematic study of linker length and rigidity," Nucleic Acids Res., 29, No. 7, Apr. 1, 1565-1573 (2001).

Lee, Y. et al., "Laser-Induced Fluorescence Detection of a Single Molecule in a Capillary", Anal. Chem., vol. 66, pp. 4142-4149 (1994).

Levene, M. et al., "Zero-Mode Waveguides for Single-Molecule Analysis at High Concentrations", Science, 299:682-686 (Jan. 2003).

Levsky et al., "Single-cell gene expression profiling," Science, 297, 836-840 (2002).

Li, H. et al., "Ultrasensitive Coincidence Fluorescence Detection of Single DNA Molecules", Anal. Chem., 75: 1664-1670 (2003).

Li, Y. et al., "Design, Synthesis, and Spectroscopic Properties of Peptide-Bridged Fluorescence Energy-Transfer Cassettes", Bioconjuate Chem., 10:241-245 (1999).

Li, Y. et al., "Structural Studies of the Klentaql DNA Polymerase", Current Organic Chem., 5:871-883 (2001).

Li, Z. et al., "A photocleavable fluorescent nucleotide for DNA sequencing and analysis", PNAS, vol. 100, No. 2, pp. 414-419 (2003).

Lin, L. et al., "Free-Space Micromachined Optical Switches for Optical Networking", IEEE J. of Selected Topics in Quanturn Electronics, vol. 5, No. 1, pp. 4-9 (Jan. 1999).

Liu, J., M.. Enzelberger, and S. Quake, "A nanoliter rotary device for polymerase chain reaction" Electrophoresis, 23(10): p. 1531-6 (2002).

Lodder, M., et al., "Misacylated Transfer RNAs Having a Chemically Removable Protecting Group." Journal of Organic Chemistry, 63(3): p. 794-803 (1998).

Loh, E. et al., "Polymerase Chain Reaction with Single-Sided Specificity: Analysis of T Cell Receptor D Chain", *Science* 243:217-220 (1989).

Lok, Corie, "Deciphering DNA, Top Speed—Helicos BioSciences aims to expedite sequencing, enable genomic medicine," *Technology Review*, pp. 27-28 (May 2005).

Lopez, G. et al., "Fabrication and Imaging of Two-Dimensional Patterns of Proteins Adsorbed on Self-Assembled Monolayers by Scanning Microscopy", *J. Arner. Chem. Soc.*, 115:10774-81 (1993).

Lotters et al., "The mechanical properties of the rubber elastic polymer polydimethylsiloxane for sensor applications," J. Micromech. Microeng., vol. 7, pp. 145-147 (1997).

Lucy et al., "Characterization of the cationic surfactant induced reversal of electroosmotic flow in capillary electrophoresis," Anal. Chem., vol. 68, pp. 300-305 (1996).

Ludwig, J and F. Eckstein, "Rapid and Efficient Synthesis of Nucleoside 5'-O-(1-Thiotriphosphates), 5'-triphosphates and 2',3'-Cyclophosphorothioates Using 2-Chloro-4H-1,3,2-benzodioxaphosphorin- 4-one." Journal of Organic Chemistry, 54(3): p. 631-635 (1989).

Lvov, Yu. et al., "Assembly of Thin Films by Means of Successive Deposition of Alternate Layers of DNA and Poly(allylamine)", *American Chemical Society, Macromolecules*, 26, pp. 5396-5399, (1993).

Macklin, J. et al., "Imaging and Time-Resolved Spectroscopy of SIngle Molecules at an Interface", *Science*, vol. 272, No. 5259, pp. 255-258 (Apr. 1996).

Maier, B., D. Bensimon, and V. Croquette, "Replication by a single DNA polymerase of a stretched single-stranded DNA." Proceedings of the National Academy of Sciences of the United States of America, 97(22): p. 12002-12007 (2000).

Marriott, G. et al., "Time resolved imaging microscopy—Phosphorescence and delayed fluorescence imaging", *Biophys, J.*, vol. 60, pp. 1374-1387 (Dec. 1991).

Marziali, A. and M. Akeson, "New DNA sequencing methods." Annual Review of Biomedical Engineering, 3: p. 195-223 (2001).

Mastrangelo, C. et al., "Vacuum-Sealed Silicon Micromachined Incandescent Light Source", *IDEM*, 89:503-506 (1989).

Meiners, J.C and S.R. Quake, "Femonewton force spectroscopy of single extended DNA molecules." Phys Rev Lett, 84(21): p. 5014-7 (2000).

Meldrum, Kevin, "Microfluidies-based products for nucleic acid analysis", http://www.americanlaboratory.com/articles/al/a9909mel.pdf, 2 pages (Sep. 1999).

Meller, A., et al., "Rapid nanopore discrimination between single polynucleotide molecules." PNAS, 97(3): p. 1079-1084 (2000).

Mertz, J. et al., "Single-molecule detection by two-photon-excited fluorescence", *Optics Letters*, vol. 20, No. 24, pp. 2532-2534 (Dec. 1995).

Metzker et al., "Elimination of residual natural nucletides from 3'-O-modified-dNTP syntheses by enzymatic mop-up," BioTechniques, 25, 814-817 (1998).

Metzker, M.L., et al., "Termination of DNA synthesis by novel 3'-modified-deoxyribonucleoside 5'-triphosphates." Nucleic Acids Res, 22(20): p. 4259-67 (1994).

Mitra, Robi, et al., "Fluorescent in situ sequencing on polymerase colonies", *Analytical Biochemistry*, 320, pp. 55-65 (2003).

Moe et al., Rapid Detection of Clinically Relevant Bacteria in Platelets Using the Hybriscan Baceterial Detection system, Journal of the American Society of Hematology, 96, No. 11, 4155 (2000).

Moore, P., "To affinity and beyong", *Nature*, vol. 426, No. 6967, pp. 725-731, (2003).

Muller et al., "Surface-micromachined microoptical elements and systems," IEEE vol. 86, No. 8, pp. 1705-1720 (1998).

Nelson, P. et al., "Bifunctional oligonucleotide probes synthesized using a novel CPG support are able to detect single base pair mutations", *NAR*, 17(18):7187-7194 (1989).

Nie, S. et al., "Probing Individual Molecules with Confocal Fluorescence Microscopy", *Science*, vol. 266, No. 5187, pp. 1018-1021 (Nov. 1994).

Nyren, P. et al., "Solid Phase DNA Minisequencing by an Enzymatic Luminometric Inorganic Pyrophosphate Detection Assay", *Anal. Biochem.*, vol. 208, pp. 171-175 (1993).

Ochman, H. et al., "Genetic Application of an Inverse Polymerase Chain Reaction", *Genetics* 120:621-623 (1988).

Ohara, To et at, "'Wired' Enzyme Electrodes for Amperometric Determination of Glucose or Lactate in the Presence ofInterfering Substances",Ana/. Chem., vol. 66, No. 15, pp. 2451-2457 (Aug. 1994).

Ohara, T. et al., "Glucose Electrodes Based on Cross-Linked Os(bpY)2CltH Complexed Poly(1-vinylimidazole) Films", *Ana/. Chem.*, vol. 65, pp. 3512-3517 (1993).

Okabe, S. et al., "Do Photobleached Fluorescent Microtubules Move?: Re-evaluation of Fluorescence Laser Photobleaching both In Vitro and in Growing Xenopus Axon", *J. Cell Bio.*, vol. 120, No. 5, pp. 1177-1186 (1993).

Ollis, D. et al., Structure of large fragment of E. coli DNA polymerase I complexed with Dtmp, *Nature*, 313:762-766 (1985).

Oroskar, A. et al., "Detection of immobilized amplicons by ELISA-like techniques" *Clin. Chem.*, 42(9):1547-1555 (1996).

Patchornik, A. et al., "Photosensitive Protecing Groups" *J. Arner. Chem. Soc.*, 92(21):6333-37 (1970).

Padmaja, T., et al., "Enzymatically degradable prodrugs: a novel methodology for drug linkage." Journal of Applied Polymer Science, 85(10): p. 2108-2118 (2002).

Pennisi, E., "Gene researchers hunt bargins, fixer-uppers." Science, 298(5594): p. 735-736 (2002).

Perales et al., "Enhancement of DNA, cDNA synthesis and fidelity at high temperatures by a dimeric single-stranded DNA-binding protein," Nucleic Acids Res., 31, No. 22, 6473-6480 (2003).

Perkins, T. et al., "Relaxation of a Single DNA Molecule Observed by Optical Microscopy", *Science*, 264:822-826 (May 1994).

Pethig, R. et at, "Applications of dielectrophoresis in biotechnology", *Tibtech*, vol. 15, pp. 426-432 (Oct. 1997).

Pisani, F. et al., "Domain Organization and DNA-Induced Conformational Changes of an Archaeal Family B DNA Polymerase", *Biochemistry*, vol. 35, pp. 9158-9166 (Jul. 1996).

Plakhotnik, T. et al, "Single-Molecule Spectroscopy", *Annu. Rev. Phys. Chem.*, vol. 48, pp. 181-212 (1997).

Ploem, J., Ch. 1 "Fluorescence Microscopy", Fluorescent and Luminescent Probes for Biological Activity, Mason, T. Ed., Academic Press, London, pp. 1-11 (1993).

Qin et al., "Elastomeric Light Valves," *Advanced Materials*, vol. 9, No. 5, pp. 407-410 (1997).

Qin, P. et al., "Site-Specific Labeling of RNA with Fluorophores and Other Structural Probes", *Methods*, vol. 18, No. 1, pp. 60-70 (May 1999).

Quake, S. et al., "Fluorescent Photobleaching Method for Sequencing DNA", pp. 1-10, circa 1996.

Quake, Stephen R. et al., "Methods and Apparatuses For Analyzing Polynucleotide Sequences", pending U.S. Appl. No. 09/707,737, filed Nov. 6, 2000.

Quake, S. et al., "Polymer Physics with Single Molecules of DNA" (Dept. of Physics), a colloquium by Stephen Quake, Stanford University, Feb. 22, 1996. (Presented at Laser Spectroscopy XII Intl. Conference, Italy, Jun. 1995.).

Quake, S. et al., "From Micro- to Nanofabrication with Soft Materials", *Science*, vol. 290, No. 5496, pp. 1536-1540 (Nov. 2000).

Rapp, R. et al., "LIGA micropump for gases and liquids", *Sensors and Actuators A*, vol. 40, pp. 57-61 (1994).

Rasolonjatovo I. and S.R. Sarfati, "6-N-(N-methylanthranyamido)-4-oxo-hexanoic acid: a new florescent protecting group applicable to a new DNA sequenceing method." Nucleosides & Nucleotides, 17(9-11): p. 2021-2025 (1998).

Rasolonjatovo, I. and Sarfati, "Development of a new DNA sequencing method: 3'-ester cleavage catalyzed by Taq DNA polymerase." Nucleosides & Nucleotides, 18(4 & 5): p. 1021-1022 (1999).

Reha-Krantz, L. et al., "Genetic and Biochemical Studies of Bacteriophage T4 DNA Polymerase 3'→5'-Exonuclease Activity", *The Journal of Biological Chemistry*, vol. 268, No. 36, pp. 27100-27108 (1993).

Reha-Krantz, L. et al., "Motif A of Bacteriophage T4 DNA Polymerase: Role in Primar Extension and DNA Replication Fidelity", *The Journal of Biological Chemistry*, vol. 269, No. 8, pp. 5635-5643 (1994).

Rigler, R, et al, "DNA-sequencing at the single molecule level." Journal of Biotechnology, 86(3): p. 161 (2001).

Rigler, R., "Fluorescence correlations, single molecule detection and large number screening—Applications in Biotechnology", *J. Biotech.*, 41: 177-186 (1995).

Ronaghi, M. et al., "A Sequencing Method Based on Real-Time Pyrophosphate", *Science,* vol. 281, pp. 363-365 (Jul. 1998).

Ronaghi, M et al., "Real-Time DNA Sequencing Using Detection of Pyrophosphate Release." *Analytical BioChemistry,* 242, No. 0432, (1996).

Rosenblum, B. et al., "New dye-labeled terminators for improved DNA sequencing patterns",*Nucleic Acids Research,* vol. 25, No. 22, pp. 4500-4504 (Nov. 1997).

Rosenblum, B. et al., "Improved single-strand DNA sizing accuracy in capillary electrophoresis", *Nucleic Acids Research,* vol. 25, No. 19, pp. 3925-3929 (Oct. 1997).

Roylance, L. et al., "A Batch-Fabricated Silicon Accelerometer", *IEEE Trans. On Elec. Dev.*, vol. ED-26, No. 12, pp. 1911-1917 (1979).

Ruparel, Hameer, "Design and synthesis of a 3'-$O$-allyl photocleavable fluorescent nucleotide as a reversible terminator for DNA sequencing by synthesis", *PNAS,* vol. 102, No. 17, pp. 5932-5937 (Apr. 26, 2005).

Ruth, J. et al., "Nucleoside Analogues with Clinical Potential in Antivirus Chemotherapy", *Molecular Pharmacology,* 20:415-422 (1981).

Sanger, F. et al., "DNA sequencing with chain-terminating inhibitors", *PNAS,* 74(12):5463-67 (Dec. 1977).

Sarfati, S.R., et al., "Synthesis of fluorescent derivatives of 3'-$O$-(6-aminohexanoyl)-pyrimidine nucleosides 5'-triphosphates that act as DNA polymerase substrates reversibly tagged at C-3'." Journal of the Chemical Society, Perkin Transactions 1: Organic and Bio-Organic Chemistry, 9: p. 1163-71 (1995).

Sato, E. et al., "Bimane Conjugates of 5-Halogenouridylic Acids as Fluorogenic Substrats for Phosphodiesterase I", *J. Chem. Research (S),* Issue 10, pp. 390-391 (1994).

Satoh, Ikuo et al., "Flow-injection determination of inorganic pyrophosphate with use of an enzyme thermistor containing immobilized inorganic pyrophosphatase", *Chemical Abstracts,* vol. 110, No. 16, pp. 409-413 (1988).

Sauer, M., et al.., "Single molecule DNA sequencing in submicrometer channels: state of the art and future prospects." Journal of Biotechnology, 86(30: p. 181-201 (2001).

Schasfoort et al., "Field-effect flow control for microfabricated fluidic networks," Science, vol. 286, pp. 942-945 (1999).

Schueller, O., et al., "Reconfiguarable diffraction gratings based on elastomeric microfluidic devices", *Sensors and Actuators,* 78, pp. 149-159 (1998).

Seeger, S. et al., "Single molecule fluorescence—High Performance Molecular Diagnosis and Screeing", translated from *BIOforum,* pp. 179-185, (Apr. 1998).

Selvin, P., "Fluorescence Resonance Energy Transfer", *Meth. In Enzymology,* vol. 246, pp. 300-335, Academic Press (1995).

Seo, Tae Seok, "Four-color DNA sequencing by synthesis on a chip using photocleavable fluorescent nucleotides", *PNAS,* vol. 102, No. 17, pp. 5926-5931 (Apr. 26, 2005).

Seo, Tae Seok, "Photocleavable fluorescent nucleotides for DNA sequencing on a chip constructed by site-specific coupling chemistry", *PNAS,* vol. 101, No. 15, pp. 5488-5493 (Apr. 13, 2004).

Shackelford, James F., "Intro. to Materials Science for Engineers,"3rd Edition, Prentice-Hall, Inc., Macmillian Publ. Co. (1992) (cited by Examiner E. Quan in related case).

Shendure et al., "Advanced sequencing technologies: Methods and goals," *Nature Reviews,* vol. 5, No. 5, pp. 335-344 (2004).

Shoji, S. et al., "Smallest Dead Volume Microvalves for Integrated Chemical Analyzing Systems", *Proceedings of Transducers '91,* IEEE, pp. 1052-1055, San Francisco (1991).

Shoji, S. e tal., "Fluids for Sensor Systems," Microsystem Technology in Chemistry and Life Science, Topics in Current Chem., vol. 194, pp. 162-188, Springer-Verlag (1998).

Smith, L. et al., "Fluorescence detection in automated DNA sequence analysis", *Nature,* vol. 321, pp. 674-679 (Jun. 1986).

Smith, L. et al., "The synthesis of oligonucleotides containing an aliphatic amino group at the 5' terminus: synthesis of fluorescent DNA primers for use in DNA sequence analysis", *Nucleic Acids Res.,* vol. 13, No. 7, pp. 2399-2412 (1985).

Smith, S. et al., "Direct Mechanical Measurements of the Elasticity of Single DNA Molecules by Using Magnetic Beads", *Science* 258:1122-26 (1992).

Smits, I., "Piezoelectric Micropump with Three Valves Working Peristaltically", *Sensors and Actuators,* vol. A21-A23, pp. 203-206 (1990).

Song et al., "Influence of the triplet excited state on the photobleaching kinetics of fluorescein in microscopy," Biophysics J., 70, 2959--2968 (1996).

Sproat, B. et al., "The synthesis of protected 5'-mercapto-2',5'-dideoxyribonucleoside- 3' -O-phosphoramidities; uses of 5-3 -mercapto-oligodeosyribonucleotides", *Nucleic Acids Res.,* 15(12):4837-48 (1987).

Stocki, S. et al., "Dynamics of Bacteriophage T4 DNA Polymerase Function: Identification of Amino Acid Residues that Affect Switching between Polymerase and and 3'→5'-Exonuclease Activities", *J. Mol. Biol.,* 254, pp. 15-28 (1995).

Strausberg, R L, e tal., "The mammalian gene collection." Science, 286(5439): p. 455-7 (1999).

Sukhorukov, G.B., et al., "Assembly of polyelectrolyte multilayer films by consecutively alternating adsorption of polynucleotides and polycations", *Thin Solid Films,* 284-285, pp. 220-223 (1996).

Tasara et al., "Incorporation of reporter molecule-labeled nucleotides by DNA polymerases. II. High-density labeling of natural DNA," Nucleic Acids Res., 31, No. 10, 2636-2646 (2003).

Taveira, N. et al., "Detection of HI VI proviral DNA by PCR and hybridization with digoxigenin labeled probes", *Mol. Cell Probes,* vol. 6, No. 4, pp. 265-270 (1992).

Taylor, D. et al., "Characterization of chemisorbed monolayers by surface potential measurements", *J. Phys. D. Appl. Phys.* 24:1443-50 (1991).

Terry, S. et al., "A Gas Chromatographic Air Analyzer Fabricated on a Silicon Wafer", *IEEE Trans. on Electron Dev.,* vol. ED-26, No. 12, pp. 1880-1886 (1979).

Theisen, P. et al., "Fluorescent dye phosphoramidite labeling of oligonucleotides", *Nucleic Acids Symp. Ser.,* vol. 27, pp. 99-100 (1992).

Thompson, N. et al., "Measuring Surface Dynamics of Biomolecules by Total Internal Reflection Fluorescence with Photobleaching Recovery or Correlation Spectroscopy", *Biophys. J.,* vol. 33, pp. 435-454 (Mar. 1981).

Thompson, N. et al., "Immunoglobulin Surface-Binding Kinetics Studies by Total Internal Reflection with Fluorescence Correlation Spectroscopy", *Biophys. J.,* vol. 43, pp. 103-114 (Jul. 1983).

Thorsen, T. S.J. Maerkl, and S.R. Quake, "Microfluidic large-scale integration." Science, 298 (5593): p. 580-4 (2002).

Tokunaga, M. et al., "Single Molecule Imaging of Fluorophores and Enzymatic Reactions Achieved by Objective-Type Total Internal Reflection Fluorescence Microscopy", *Biochem. And Biophys. Res. Comm.,* vol. 235, pp. 47-53 (1997).

Toneguzzo, F. et al., "Use of a Chemically Modified T7 DNA Polymerase for Manual and Automated Sequencing Super coiled DNA", *BioTech,* vol. 6, No. 5, pp. 460-469 (1988).

Trager, R. S., "DNA sequencing—Venter's next goal: 1000 human genomes." Science, 298(5595): p. 947 (2002).

Tufte, O. et al., "Silicon Diffused-Element Piezoresistive Diaphragms", *J. Applied Phys.,* vol. 31, No. 11, pp. 3322-3327 (Nov. 1962).

Tyagi, S. et al., "Multicolor molecular beacons for allele discrimination", *Nat. Biotechnol.,* 16:49-53 (1998).

Ullman's Encyclopedia of industrial Chemistry, 61D Edition, vol. 6, Sections 6 to 6.3, Subject: Carbon Black, Wiley-VCH (1999).

Unger et al., "Monolithic microfabricated valves and pumps by multilayer soft lithography," Science 288: 113-116 (2000).

Unger, M. et al., "Single-Molecule Fluorescence Observed with Mercury Lamp Illumination", *Biotechniques,* vol. 27, PD. 1008-1014 (Nov. 1999).

Vale, R. et al., "Direct observation of single kinesin molecules moving along microtubules", *Nature*, vol. 380, pp. 451-453, (Apr. 1996).

Van Dam, R.M. and S.R Quake, "Gene expression analysis with universal n-mer arrays." Genome Res, 12(1): p. 145-52 (2002).

Van De Pol, F. et al., "Micro-liquid handling devices: A Review", Micro System Technologies 90, 1st Intl. Conf. On Micro Electro, Opto, Mechanic Systems and Components, pp. 799-805, Berlin, Springer-Verlag, (1990).

Van Oijen et al., "Single molecule kinetics of λ exonuclease reveal base dependence and dynamic disorder," Science, 301, 1235-1238 (2003).

Venter, J.L., et al., "The sequence of the human genome," Science, 291(5507): p. 1304-1351 (2001).

Vieider, C. et al., "A Pneumatically Acutated Micro Valve With A Silicone Rubber Membrane For Integration With Fluid-Handling Systems", *Proceedings of Transduces '95*, pp. 284-286, Stockholm (1995).

Walker, M.G., et al., "Prediction of gene function by genome-scale expression analysis: Prostate cancer-associated genes.": Genome Researce, 9(12): p. 1198-1203 (1999).

Wang, G. et al., "Design and Synthesis of New Fluorogenic HIV Protease Substrates Based on Resonance Energy Transfer", *Tetrahedron Lett.*, 31(45):6493-96 (1990).

Wang, M.D., et al., "Force and Velocity measured for single molecules of RNA polymerase." Science, 282(5390): p. 902-907 (1998).

Washizu et al., "Molecular dielectrophoresis of biopolymers," IEEE Transactions on Industry Applications, vol. 30, No. 4, pp. 835-843 (1994).

Watkins, R. et al., "A Total Internal-Reflection Technique for the Examination of Protein Adsorption", *J. Biomed. Mater. Res.*, vol. 11, pp. 915-938 (1977).

Weber, J.L. and E.W. Myers, "Human whole-genome shotgun sequencing." Genome Research, 7(5): p. 401-409 (1997).

Webster, J. et al., "Monolithic Capillary Gel Electrophoresis Stage with On-Chip Detector", Intl. Conf. on MEMS (MEMS 96), pp. 491-496 (1996).

Wedekind, P. et al., "Scanning microphotolysis: a new photobleaching technique based on fast intensity modulation of a scanned laser beam and confocal imaging", *J. Microscopy*, vol. 176, Pt. 1, pp. 23-33 (Oct. 1994).

Weir, et al., "Hybrigel Purification: A Novel Technique for Accelerated Prepration of DNA Sequence Products for Capillary Electrophoresis and Multiplexing," Clinical Chemistry, vol. 45, No. 11, p. 2052 (1999).

Weiss, S., "Fluorescence Spectroscopy of Single Biomolecules", *Science*, vol. 283, pp. 1676-1683 (Mar. 1999).

Welch, M.B. and K. Burgess, "Synthesis of fluorescent, photolabile 3'-O-protected nucleoside triphosphates for the base addition sequencing scheme," Nucleosides & Nucleotides, 18(2): p. 197-201 (1999).

Werner et al "Progress towards single-molecule DNA sequencing: a one color demonstration." J Biotechnol, 102(1): p. 1-14 (2003).

Williams, N. et al., "Exploring the Adenine Nucleotide Binding Sites on Mitochondrial $F_1$-ATPase with a New Photoaffinity Probe, 3'-O-(4-Benzoyl)benzoyl Adenosine 5'-Triphosphate", *J. Bioi. Chem.*, 237(6):2834-41 (1982).

Winter et al., "Direct gene expression analysis," Curr. Pharm. Biotech., 5, p. 191-197 (2004).

Wu, et al., "Synthesis and Properties of Adenosine-5'-triphosphoro-γ-1-(5-sulfonic acid)naphthyl Ethylamide: A Fluorescent Nucleotide Substrate for DNA-Dependent RNA Polymerase from *Escherichia coli*," Archives of Biochemistry and Biophysics, vol. 246, No. 2, pp. 564-571 (1986).

Wuite, G. et al., "Single-molecule studies of the effect of template tension on T7 DNA polymerase activity", *Nature*, 404:103-6 (2000).

Xia et al., "Complex optical surfaces formed by replica molding against elastomeric masters," Science vol. 273, pp. 347-349 (1996).

Xia et al. "Soft Lithography," Angew. Chem. Int. Ed. vol. 37, pp. 550-575 (1998).

Xia, G., e tal., "Directed evolution of novel polymerase activities: mutation of a DNA polymerase into a efficient RNA polymerase." Proc Natl Acad Sci USA; 99(10) p. 6597-6602 (2002).

Xie, "Single molecule approach to dispersed kinetics and dynamic disorder: Probing conformational fluctuation and enzymatic dynamics," J. Chem. Physics, 117, No. 24, p. 11024-11032 (2002).

Xu, X. et al., "Direct Measurement of Single-Molecule Diffusion and Photodecomposition in Free Solution", *Science*, vol. 275, pp. 1106-1109, (Feb. 1997).

Xu, X. et al., "Long-Range Electrostatic Trapping of Single-Protein Molecules at a Liquid-Solid Interface", *Science*, vol. 281, pp. 1650-1653 (Sep. 1998).

Yang et al., "A Mems Thermopneumatic Silicone Rubber Membrane Valve", Proceedings of IEEE 10th Annual International Workshop on MicroElectro Mechanical Systems, Sensors and Actuators, vol. A64, No. 1, pp. 101-108 (1998).

Yazdi, N. et al., "Micromachined Inertial Sensors", *Proceedings of the IEEE*, vol. 86, No., pp. 1640-1659 (Aug. 1998).

Yershov, G. et al., "DNA analysis and diagnostics on oligonucleotide microchips", *Proc. Natl. Acad.* Sci. USA, vol. 93, pp. 4913-4918 (May 1996).

Young et al., "Contoured elastic-membrane microvalves for microfluidic network integration," J. Biomechaincal Engineering, vol. 121, pp. 2-6 (1999).

Yu., et al., "Cyanine dye dUTP analogs for enzymatic labeling of DNA probes." Nucleic Acids Res, 22(15): p. 3226-32 (1994).

Zdeblick, M. et al., "A Microminiature Electric-To-Fluidic Valve", Transducers '87, reprinted in *Micromechanics and MEMS Classic and Seminal Papers to 1990*, IEEE Press, pp. 437-439 (1987).

Zhu, Z. et al., "Molecular Mechanism Controlling the Incorporation of Fluorescent Nucleotides into DNA by PCR", *Cytometry*, 28:206-211 (1997).

Zhu, Z. et al., "Directly labeled DNA probes using fluorescent nucleotides with different length linkers", *Nucleic Acids Res.*, vol. 22, No. 16, pp. 3418-3422 (1994).

Zuckerman, R. et al., "Efficient methods for attachment of thiol specific probes to the 3' ends of synthetic oligodeoxyribonucleotides", *Nucleic Acids Res.*, 15(13):5305-5321 (1987).

Therminator DNA Polymerase FAQ, http://www.neb.com/nebecomm/products/faqproductM0261.asp downloaded Jun. 1, 2005, 1 page.

\* cited by examiner

DXS17 BASED PRIMER:

TEMPLATE 10 → 3'-Biotin-TEG-TTT TTT TTT GGG GAA TAG GTG AAT AGG AAA tga cag cga tcg act gcg tcg act PRIMER 12 → 5'-Biotin-TEG-aaa aaa aaa aaa CCC CTT ATG CAC TTA TCC TTT

FIG. 2

'9 LNA' INCORPORATED PRIMERS:

DXS17 PRIMER
5'-NH₂-cCc CtT aTg CaC tTa TcC ttt

7G7A PRIMER
5'-NH₂-gTc TgG gCt TtT gGt TtC tgg g

377 PRIMER
5'-NH₂-cTt GcA tcc Atc cTc TgC cct g

FIG. 3

LNA

SEQUENCE LISTING

```
<160> NUMBER OF SEQ ID NOS: 7

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaaaacccct tatgcactta tcctttact                                           29

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tcagctgcgt cagctagcga cagtaaagga taagtgcata aggggttttt                    50

<210> SEQ ID NO 3
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcagctgcgt cagctagcga cagtaaagga taagtgcata aggggttttt ttttttt           57

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 4
aaaaaaaaaa aacccttat gcacttatcc ttt                33

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 cccctttatgc acttatcctt t                           21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtctgggctt ttggtttctg gg                           22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cttgcatcca tcctctgccc tg                           22
```

STABILIZING A NUCLEIC ACID FOR NUCLEIC ACID SEQUENCING

TECHNICAL FIELD OF THE INVENTION

The invention provides methods for sequencing a nucleic acid comprising stabilizing a primer/target nucleic acid duplex attached to a substrate. Generally, methods of the invention comprise the use of a dual-anchored primer/target nucleic acid duplex or stabilizing molecule.

BACKGROUND OF THE INVENTION

Completion of the human genome has paved the way for important insights into biologic structure and function. Knowledge of the human genome has given rise to inquiry into individual differences, as well as differences within an individual, as the basis for differences in biological function and dysfunction. For example, single nucleotide differences between individuals, called single nucleotide polymorphisms (SNPs), are responsible for dramatic phenotypic differences. Those differences can be outward expressions of phenotype or can involve the likelihood that an individual will get a specific disease or how that individual will respond to treatment. Moreover, subtle genomic changes have been shown to be responsible for the manifestation of genetic diseases, such as cancer. A true understanding of the duplexities in either normal or abnormal function will require large amounts of specific sequence information.

An understanding of cancer also requires an understanding of genomic sequence duplexity. Cancer is a disease that is rooted in heterogeneous genomic instability. Most cancers develop from a series of genomic changes, some subtle and some significant, that occur in a small subpopulation of cells. Knowledge of the sequence variations that lead to cancer will lead to an understanding of the etiology of the disease, as well as ways to treat and prevent it. An essential first step in understanding genomic duplexity is the ability to perform high-resolution sequencing.

Various approaches to nucleic acid sequencing exist. One conventional way to do bulk sequencing is by chain termination and gel separation, essentially as described by Sanger et al., Proc. Natl. Acad. Sci., 74(12): 5463–67 (1977). That method relies on the generation of a mixed population of nucleic acid fragments representing terminations at each base in a sequence. The fragments are then run on an electrophoretic gel and the sequence is revealed by the order of fragments in the gel. Another conventional bulk sequencing method relies on chemical degradation of nucleic acid fragments. See, Maxam et al., Proc. Natl. Acad. Sci., 74: 560–564 (1977). Finally, methods have been developed based upon sequencing by hybridization. See, e.g., Drmanac, et al., Nature Biotech., 16: 54–58 (1998).

Bulk sequencing techniques are not useful for the identification of subtle or rare nucleotide changes due to the many cloning, amplification and electrophoresis steps that complicate the process of gaining useful information regarding individual nucleotides. The ability to sequence and gain information from single molecules obtained from an individual patient is the next milestone for genomic sequencing. As such, research has evolved toward methods for rapid sequencing, such as single molecule sequencing technologies.

There have been many proposals to develop new sequencing technologies based on single-molecule measurements, generally either by observing the interaction of particular proteins with DNA or by using ultra high resolution scanned probe microscopy. See, e.g., Rigler, et al., *DNA-Sequencing at the Single Molecule Level*, Journal of Biotechnology, 86(3): 161 (2001); Goodwin, P. M., et al., *Application of Single Molecule Detection to DNA Sequencing*. Nucleosides & Nucleotides, 16(5–6): 543–550 (1997); Howorka, S., et al., *Sequence-Specific Detection of Individual DNA Strands using Engineered Nanopores*, Nature Biotechnology, 19(7): 636–639 (2001); Meller, A., et al., *Rapid Nanopore Discrimination Between Single Polynucleotide Molecules*, Proceedings of the National Academy of Sciences of the United States of America, 97(3): 1079–1084 (2000); Driscoll, R. J., et al., *Atomic-Scale Imaging of DNA Using Scanning Tunneling Microscopy*. Nature, 346(6281): 294–296 (1990). Unlike conventional sequencing technologies, their speed and read-length would not be inherently limited by the resolving power of electrophoretic separation. Other methods proposed for single molecule sequencing include detecting individual nucleotides as they are incorporated into a primed template, i.e., sequencing by synthesis.

While single molecule techniques have several advantages, implementation has been problematic. For example, the reproducibility and accuracy of many single molecule techniques rely upon the stability of a primer/target nucleic acid duplex attached to a solid substrate. However, incomplete binding of the primer to the template, disengagement of the primer from the template and disengagement of the duplex from the substrate are frequent occurrences in such single molecule techniques.

Accordingly, there is a need in the art for methods and devices for sequencing generally, and single molecule sequencing in particular, including methods for stabilizing a target nucleic acid for sequence determination.

SUMMARY OF THE INVENTION

The invention generally provides methods and surfaces for nucleic acid sequencing comprising stabilized primer/target nucleic acid duplexes on a surface. Methods of the invention generally contemplate the use of a primer/target nucleic acid duplex in which each of the primer and the template contain a molecule having a binding partner on the substrate. The primer/target is stabilized on the surface by binding of both the primer and the template to the surface. Binding pairs for use in the invention are any molecular pair that can be bound to a surface and attached to a nucleic acid. Some examples of preferred pairs include ligand/receptor, affinity pairs, antigen/antibody, and carbohydrate/lectin. For example, biotin/streptavidin, digoxigenin/anti-digoxigenin, and dinitrophenol/anti-dinitrophenol perform well in the invention. Other pairs are apparent to the skilled artisan based upon the description of the invention provided below.

According to the invention, the primer contains a member of a binding pair at its 5' terminus, and the template contains a member of a binding pair at its 3' terminus or the primer contains a member of a binding pair at its 3' terminus and the template contains a member of a binding pair at its 5' terminus. Thus, the primer hybridizes to the template, and the two attached binding pair members are oriented to bind to their respective mates on the surface.

The template and primer may contain the same type or species of binding pair or they may contain separate types or species. Binding may occur to a single species of binding partner or to separate members of the same species. For example, in one embodiment, both the template and the primer are bioinylated at opposite ends oriented to the surface (i.e., one at the 3' end and one at the 5' end) and the two biotin molecules adhere to the same streptavidin molecule (which has capacity to bind four biotins) on the surface. Alternatively, the two biotins adhere to separate streptavidin molecules spaced closely together on the surface. In another embodiment, the primer is attached to a member of a first binding pair and the template is attached to a member of a second binding pair. Upon hybridization, the first member attaches to its mate on the surface, and the second member attaches to its separate mate on the surface. In either embodiment, the combination of two separate mating pairs reduces loss of the hybrid due to either the template or the primer dissociating. It is apparent to the skilled artisan based upon this disclosure that any combination of binding pairs works to stabilize hybrid binding to a surface. For example, template and primer may have attached separate species of binder that, although distinct, bind to the same surface-bound mate.

The invention comprises methods for sequencing nucleic acids using stabilized, support-bound primer/template hybrids as described above. In a preferred embodiment, methods of the invention comprise template-dependent sequencing by synthesis using a polymerase capable of adding nucleotides to the primer in a template-dependent fashion. The invention is particularly useful for single molecule nucleic acid sequencing in which primer/template duplex is attached to a substrate such that the duplex is individually optically resolvable. Individual strand sequence is determined by detecting ordered template-dependent nucleotide incorporation into the primer and compiling a sequence of the template based upon the order of incorporated nucleotides.

The invention also provides for the use of a stabilizing molecule in template-dependent sequencing. Stabilizing molecules useful in the invention include, for example, locked nucleic acid ("LNA") analogs and peptide nucleic acid ("PNA") analogs. Generally, a stabilizing molecule increases the affinity and specificity of the primer/target nucleic acid bond, and increases the melting temperature of the primer/target nucleic acid duplex or the specificity of incorporation of a nucleotide into the primer in a sequencing by synthesis reaction. An example of a locked nucleic acid is shown in FIG. 4. Both locked nucleic acid and peptide nucleic acid analogs increase the melting temperature of the primer/template duplex and, therefore, confer stability on the hybrid, whether or not the anchoring strategies described above are used.

Polymerases useful in the invention include any polymerizing agent capable of catalyzing a template-dependent addition of a nucleotide or nucleotide analog to a primer. Depending on the characteristics of the target nucleic acid, a DNA polymerase, an RNA polymerase, or a reverse transcriptase can be used. According to one aspect of the invention, a thermophilic polymerase is used, such as ThermoSequenase®, 9° N™, Taq, Tfl, Tth, Tli, Therminator, or Pfu. In one embodiment, the invention provides for the primer/target nucleic acid duplex to be exposed to the polymerase and nucleotide at a temperature between about 30° and about 80° Celsius. A preferred polymerase is a Klenow fragment having reduced 3'-5' exonuclease activity.

Nucleotides useful in the invention include any nucleotide or nucleotide analog, whether naturally-occurring or synthetic. For example, preferred nucleotides are adenine, cytosine, guanine, uracil, or thymine bases; xanthine or hypoxanthine, 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, locked nucleic acids and any other structural moiety that can act substantially like a nucleotide or base, for example, by exhibiting base-complementarity with one or more bases that occur in DNA or RNA and/or being capable of base-complementary incorporation, and includes chain-terminating analogs.

Nucleotides for primer addition according to the invention preferably comprise a detectable label. Labeled nucleotides include any nucleotide that has been modified to include a label that is directly or indirectly detectable. Preferred labels include optically-detectable labels, including fluorescent labels or fluorophores, such as fluorescein, rhodamine, derivatized rhodamine dyes, such as TAMRA, phosphor, polymethadine dye, fluorescent phosphoramidite, Texas Red, green fluorescent protein, acridine, cyanine, cyanine 5 dye, cyanine 3 dye, 5-(2'-aminoethyl)-aminonaphthalene-1-sulfonic acid (EDANS), BODIPY, 120 ALEXA or a derivative or modification of any of the foregoing, and also include such labeling systems as hapten labeling. Accordingly, methods of the invention further provide for exposing the primer/target nucleic acid duplex to a digoxigenin, a fluorescein, an alkaline phosphatase or a peroxidase.

In one embodiment, fluorescence resonance energy transfer (FRET) is used to determine the base type incorporated into the primer. Fluorescence resonance energy transfer in the context of sequencing is described generally in Braslavasky et al., *Sequence Information can be Obtained from Single DNA Molecules*, Proc. Nat'l Acad. Sci., 100: 3960–3964 (2003), incorporated by reference herein. Essentially, in one embodiment, a donor fluorophore is attached to either the primer, polymerase, or template. Nucleotides added for incorporation into the primer comprise an acceptor fluorophore that is activated by the donor when the two are in proximity. Activation of the acceptor causes it to emit a characteristic wavelength of light and also quenches the donor. In this way, incorporation of a nucleotide in the primer sequence is detected by detection of acceptor emission. Of course, nucleotides labeled with a donor fluorophore also are useful in methods of the invention; FRET-based methods of the invention only require that a donor and acceptor fluorophore pair are used, a labeled nucleotide may comprise one fluorophore and either the template or the polymerase may comprise the other. Such labeling techniques result in a coincident fluorescent emission of the labels of the nucleotide and the labeled template or polymerase, or alternatively, the fluorescent emission of only one of the labels.

In a preferred embodiment, after detection, the label is rendered undetectable by removing the label from the nucleotide or extended primer, neutralizing the label, or masking the label. In certain embodiments, methods according to the invention provide for neutralizing a label by photobleaching. This is accomplished by focusing a laser with a short laser pulse, for example, for a short duration of time with increasing laser intensity. In other embodiments, a label is photocleaved. For example, a light-sensitive label bound to a nucleotide is photocleaved by focusing a particular wavelength of light on the label. Generally, it may be preferable to use lasers having differing wavelengths for exciting and photocleaving. Labels also can be chemically cleaved. Labels may be removed from a substrate using reagents, such as NaOH or other appropriate buffer reagent.

Preferred substrates include glass, silica, and others with the optical properties described herein. Surfaces for sequencing according to the invention may be coated with, for example, an epoxide, polytetrafluoroethylene or a derivative of polytetrafluoroethylene, such as silanized polytetrafluoroethylene, a polyelectrolyte multilayer (PEM), or the equivalent.

Primers useful in the invention hybridize to template in a manner that allows template-dependent sequencing-by-synthesis. Depending on the target nucleic acid, the primer may comprise DNA, RNA or a mixture of both. The invention also teaches the use of stabilizing molecules used in connection with the primer or the primer/template duplex, such as locked nucleic acid or peptide nucleic acid analogs. According to the invention, the melting temperature of the primer/target nucleic acid duplex may be increased from about 3° to about 8° Celsius per PNA or LNA base included in the primer. In one embodiment, the primer comprises a locked nucleic acid base on its 3' terminus. The primer may comprise any portion of PNA or LNA bases, such as between about 10% and about 50%, more than about 50%, or less than about 10%, 20%, 30%, 40%, 50% or 60% of the total nucleic acid residues in the primer. The PNA or LNA bases may be consecutive in the primer or may be interspersed throughout the primer. In a preferred embodiment, PNA or LNA bases are spaced apart at a distance of at least one turn of the helix when the primer is hybridized to template. The use of LNA or PNA analogs allows primers to be shorter than would be the case to achieve similar melting temperatures using conventional nucleic acids. According to one embodiment of the invention, the primer comprises fewer than 25 nucleic acids.

Methods of the invention are suitable for de novo sequencing, re-sequencing, sequence analysis, DNA fingerprinting, polymorphism identification, for example single nucleotide polymorphisms (SNP) detection, as well as for research and clinical applications in genetics. Applied to RNA sequences, methods according to the invention also identify alternate splice sites, enumerate copy number, measure gene expression, identify unknown RNA molecules present in cells at low copy number, annotate genomes by determining which sequences are actually transcribed, determine phylogenic relationships, and elucidate differentiation of cells. Methods and surfaces of the invention are useful in diagnostic, therapeutic, prognostic (including drug selection), and developmental applications.

As will be appreciated by one skilled in the art, individual features of the invention may be used separately or in any combination. A detailed description of embodiments of the invention is provided below. Other embodiments of the invention are apparent upon review of the detailed description that follows.

BRIEF DESCRIPTION OF THE DRAWINGS

FIG. 2 depicts a primer (SEQ ID NO: 4) and target nucleic acid (SEQ ID NO: 3) biotinylated to align complementary nucleotides.

FIG. 3 depicts three primers (SEQ ID NOS 5–7, respectively in order of appearance) comprising locked nucleic acid bases.

DETAILED DESCRIPTION

Figure 1:
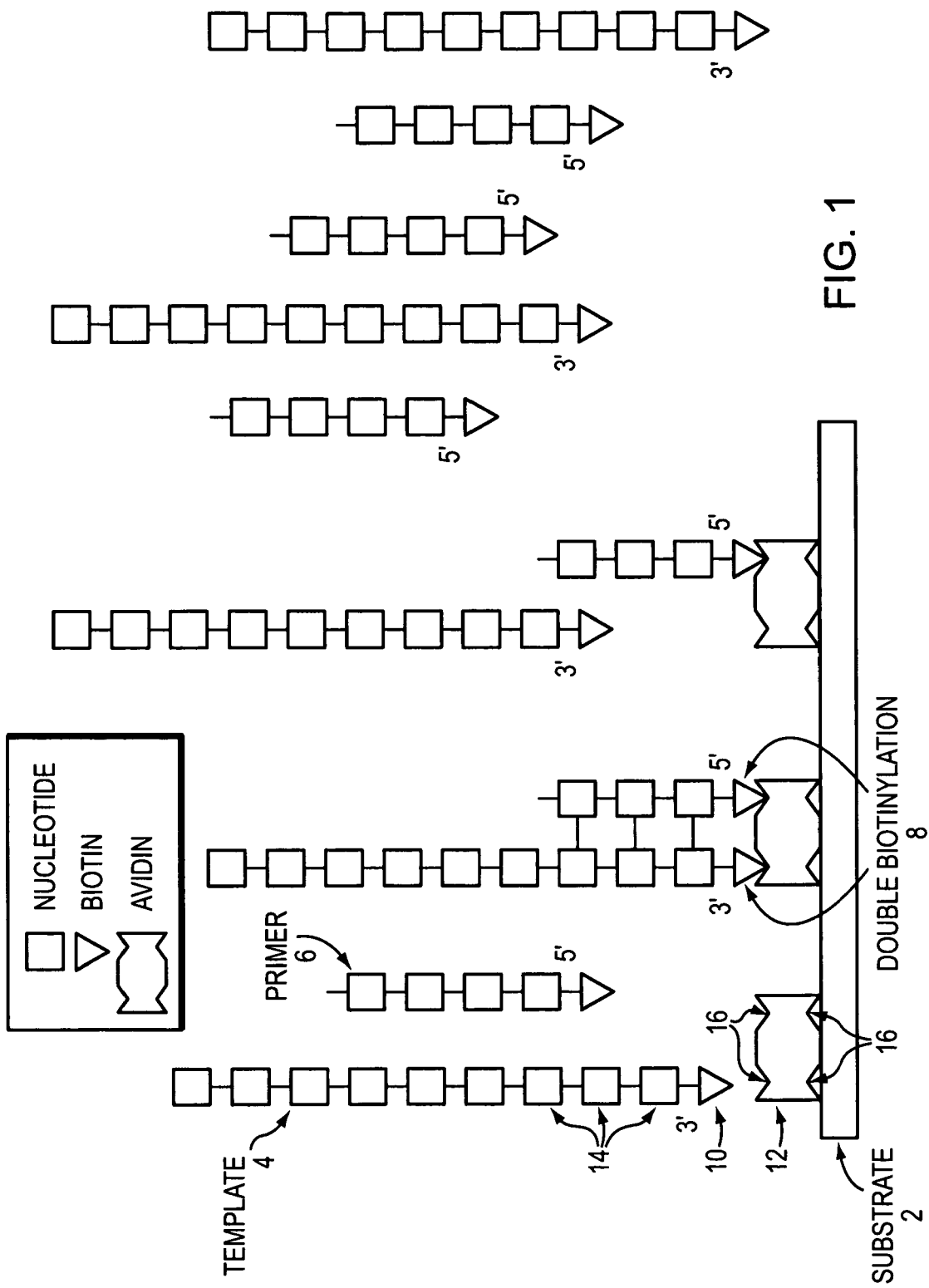
FIG. 1 depicts a dual biotinylation reaction securing a primer and target nucleic acid to a substrate.

The results of single molecule sequencing are influenced by the stability of substrate-bound primer/target nucleic acid duplexes. Typically, single molecule sequencing comprises repeated single base extension reactions followed by one or more wash steps. Sequencing occurs on single strands spaced apart such that each strand is individually optically resolvable. Spatial and temporal stability of the individual strands are important in order to preserve the integrity of the sequencing process. One way in which the spatial stability of a single molecule array can be disrupted is if the template and/or primer become disassociated with the surface. For example, template/primer hybridization is a dynamic process. Primer melts off template at a low, but detectable rate. Once melting occurs, at least some portion of primer will be unavailable to re-anneal with template. That is not necessarily a problem in a bulk sequencing reaction in which numerous copies of each template are available for sequencing. However, in single molecule sequencing, in which individual strands are sequenced, loss of any strand can have a significant effect on the result. Methods and surfaces of the invention address this problem by placing stabilizing binding partners on each of the template and primer and, optionally, utilizing stabilizing molecules that confer an increased melting temperature on the primer/template hybrid.

I. General Considerations

Substrates

Generally, a substrate may be made of any suitable material that allows single molecules to be individually optically resolvable. Substrates for use according to the invention can be two- or three-dimensional and can comprise a planar surface (e.g., a glass slide) or can be shaped. Appropriate substrates include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silica, metal (e.g., alkanethiolate-derivatized gold), cellulose, nylon, latex, dextran, gel matrix (e.g., silica gel), polyacrolein, or composites.

Preferably, a substrate used according to the invention includes a biocompatible or biologically inert material that is transparent to light and optically that (i.e., with a minimal micro-roughness rating). Specially manufactured, or chemically derivatized, low background fluorescence substrates (e.g., glass slides) are also contemplated according to the invention. Substrates may be prepared and analyzed on either the top or bottom surface of the planar substrate (i.e., relative to the orientation of the substrate in the detection system).

The invention also includes three-dimensional substrates such as spheres, tubes (e.g., capillary tubes), microwells, microfluidic devices, or any other structure suitable for anchoring a nucleic acid. For example, a substrate can be a microparticle, a bead, a membrane, a slide, a plate, a micromachined chip, and the like. Substrates can include planar arrays or matrices capable of having regions that include populations of target nucleic acids or primers. Examples include nucleoside-derivatized CPG and polystyrene slides; derivatized magnetic slides; polystyrene grafted with polyethylene glycol; and the like.

Factors for selecting substrates include, for example, the material, porosity, size, and shape. Other important factors to be considered in selecting appropriate substrates include size uniformity, efficiency as a synthesis support, and the substrate's optical properties, e.g., clear smooth substrates (free from defects) provide instrumentational advantages when detecting incorporation of nucleotides in single molecules (e.g., nucleic acids.).

Substrates are coated with a surface that facilitates nucleic acid binding and that reduces background. Preferred coatings are epoxides, silanized epoxides, biotinylated epoxides, streptavidinated epoxides, polyelecrolyte multilayers, including those that are derivatized for nucleic acid attachment (e.g., biotinylated, streptavidinated, or coated with a binding partner on the template/primer.

Surfaces

Surfaces used to attach duplexes according to the invention can be any surface to which a binding partner is capable of attaching. For sequencing, surfaces should be free of debris, especially debris capable of fluorescing. Also, surfaces should be stable and transparent to light. Preferred surfaces are epoxy surfaces and polyelectrolyte multilayer surfaces. Either of those surfaces is easily derivatized as described in the art for attachment of binding pairs. For example, epoxide surfaces are derivatized with silane or other species capable of receiving binding partners. In certain embodiments, binding pair members attached to template/primer hybrids attach directly to the surface via a molecule embedded in the surface that is not the normal binding partner for the binding pair member. Polyelectrolyte multilayer surfaces are formed from a variety of alternating layers of positive and negative charge. Preferred polyelectrolyte multilayer surfaces are described in detail below.

Target Nucleic Acids

A target nucleic acid for analysis may be obtained from a patient sample, e.g., from blood, urine, cerebrospinal fluid, seminal fluid, saliva, breast nipple aspirate, sputum, stool and biopsy tissue. Any tissue or body fluid specimen may be used according to methods of the invention.

A target nucleic acid can come from a variety of sources. For example, nucleic acids can be naturally occurring DNA or RNA isolated from any source, recombinant molecules, cDNA, or synthetic analogs, as known in the art. For example, the target nucleic acid may be genomic DNA, genes, gene fragments, exons, introns, regulatory elements (such as promoters, enhancers, initiation and termination regions, expression regulatory factors, expression controls, and other control regions), DNA comprising one or more single-nucleotide polymorphisms (SNPs), allelic variants, and other mutations. Also included is the full genome of one or more cells, for example cells from different stages of diseases such as cancer. The target nucleic acid may also be mRNA, tRNA, rRNA, ribozymes, splice variants, antisense RNA, or siRNA. Also contemplated according to the invention are RNA with a recognition site for binding a polymerase, transcripts of a single cell, organelle or microorganism, and all or portions of RNA complements of one or more cells, for example, cells from different stages of development or differentiation, and cells from different species. Nucleic acids can be obtained from any cell of a person, animal, plant, bacteria, or virus, including pathogenic microbes or other cellular organisms. Individual nucleic acids can be isolated for analysis.

Stabilizing Molecules and Primers

Methods of the invention also contemplate using a stabilizing molecule in a sequencing-by-synthesis reaction. The stabilizing molecule strengthens the primer/template bond and increases the specificity of incorporation of nucleotides into the primer, the melting temperature of the primer/target nucleic acid duplex, or both. A stabilizing molecule may comprise nucleotide or internucleotide analogs, or covalently bound minor groove binders or intercalators that enhance hybridization avidity or specificity of the primer to a target nucleic acid. The internucleotide analogs can comprise one or more of a phosphate ester analog such as alkyl phosphonates, phosphoroamidates, alkylphosphotriesters, phosphorothioates and phosphorodithioates.

In one aspect, the stabilizing molecule comprises a minor groove binder. Minor groove binders are described in detail in U.S. Pat. No. 6,084,102 which is incorporated by reference in its entirety herein. Generally, a minor groove binder has a molecular weight of approximately 150 to approximately 2000 daltons, and typically covalently attaches to at least one of the nucleotides in a duplex. It incorporates into a duplex to strengthen the template/primer bond, thus increasing hybridization stability.

In one embodiment, a stabilizing molecule may comprise a conformationally restricted nucleotide analog such as a peptide nucleic acid base, a locked nucleic acid base or an oxetane modified base (for a discussion of base constraining oxetane modifications, see U.S. Published Patent Application No. 20040142946, the disclosure of which is incorporated by reference herein). A peptide nucleic acid is a nucleic acid analog in which the backbone comprises synthetic peptide like linkages (amide bonds) usually formed from N-(2-amino-ethyl)-glycine units, resulting in an achiral and uncharged molecule. PNA hybridizes with complementary nucleic acids with high affinity and specificity, and forms PNA/DNA and PNA/RNA duplexes having greater thermal and chemical stability than counterpart DNA/DNA duplexes.

Figure 4:
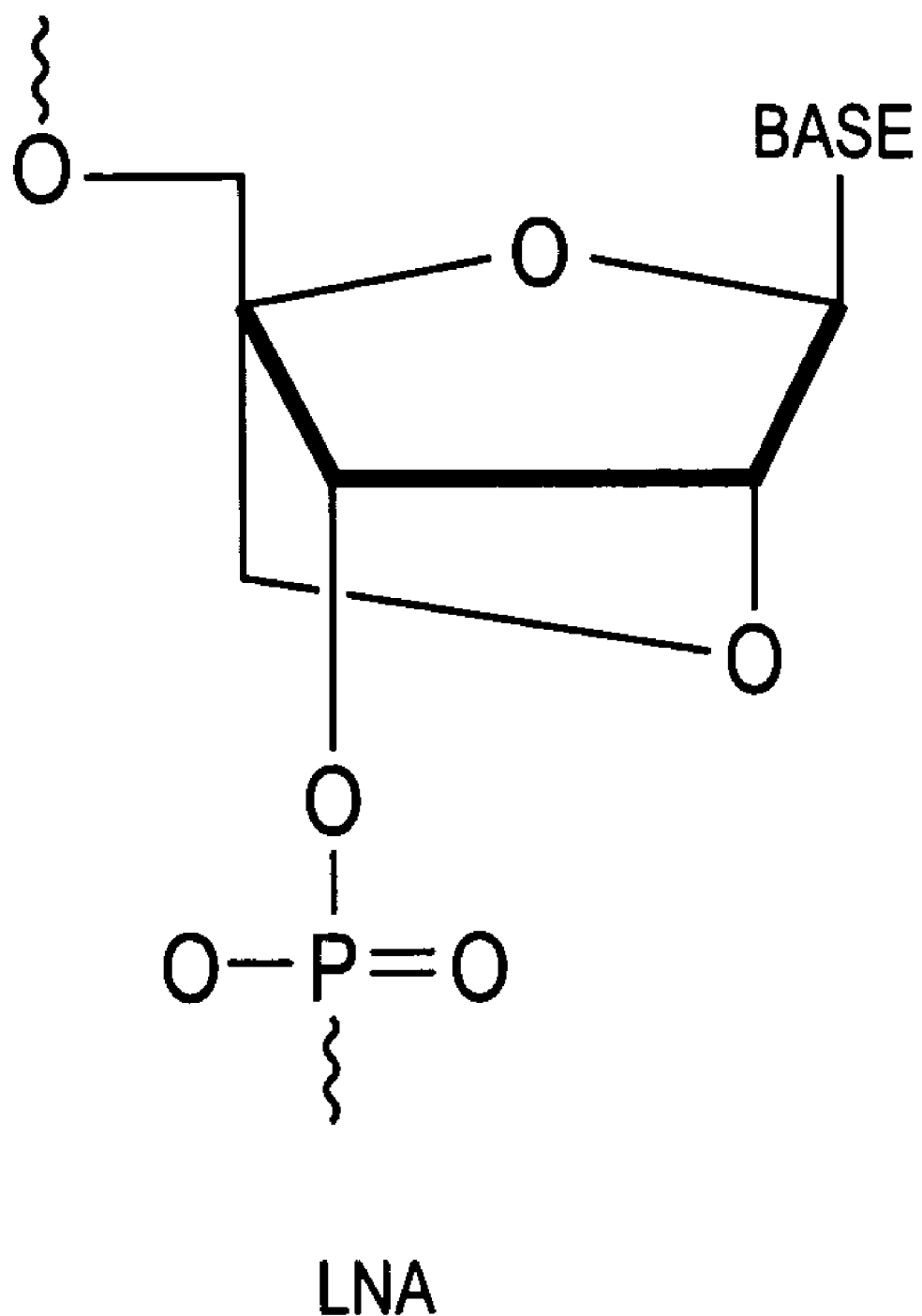
FIG. 4 depicts the structure of a locked nucleic acid base.

A locked nucleic acid is a bicyclic nucleic acid analog that contains one or more 2'-O, 4'-C methylene linkage(s), which effectively locks the furanose ring in a C3'-endo conformation. This methylene linkage "bridge" restricts the flexibility of the ribofuranose ring and locks the structure into a rigid bicyclic formation. Because of its unique structural conformation, locked nucleic acids demonstrate a much greater affinity and specificity to their complementary nucleic acids than do natural DNA counterparts and increases the thermal and chemical stability of a primer/target nucleic acid duplex. LNAs will hybridize to complementary nucleic acids even under adverse conditions, such as under low salt concentrations and in the presence of chaotropic agents. According to one aspect of the invention, locked nucleic acids increase the melting point of the primer/target nucleic acid duplex by about 3° to about 8° Celsius per locked nucleic acid base incorporated in the primer. FIG. 4 shows an example of the structure of a locked nucleic acid base.

Depending on the target nucleic acid, the primer may comprise DNA, RNA or a mixture of both. Locked nucleic acid bases may be interspersed throughout a strand of a primer, as shown in FIG. 3, or may be placed consecutively or singularly in predetermined locations. The amount and placement of the locked nucleic acid bases depends on the desired characteristics of the primer. In one embodiment, the primer comprises a locked nucleic acid base at its 3' terminus. The primer may comprise any portion of locked nucleic acid bases, such as between about 10% and about 50%, more than about 50%, or less than about 10%, 20%, 30%, 40%, 50% or 60% of the total bases in the primer.

In general, primer length is selected to facilitate hybridization to a sufficiently complementary region of the template nucleic acid downstream of the region to be analyzed. The exact lengths of the primers depend on many factors, including temperature and source of primer. Placement of locked nucleic acid bases throughout a primer allows for an increased melting temperature of the primer/target nucleic acid duplex during a sequencing reaction. This also allows the primer length to remain short compared to a primer that does not contain locked nucleic acid bases. Embodiments of this invention include primers with 20 bases or less, which incorporate from 1 to 12 or more locked nucleic acid bases. For example, a 20 base primer which includes 12 locked nucleic acid bases may yield a melting temperature of between about 80° to 90° C. According to one embodiment of the invention, the primer comprises less than about 30, 25, 20, 15, 10, or 5 bases.

FIG. 3 shows three exemplary primers (DXS17, 7G7A, and 377), each containing nine locked nucleic acids and comprising a sequence complementary to a known primer attachment site of a target nucleic acid. While FIG. 3 shows primers of known sequences complementary to a known region of a template, primers useful in the invention also include primers comprising a random sequences. Useful primers also include primers comprising a sequence that is complementary to a known priming region that has been ligated to a target nucleic acid.

Primers can be synthetically made using conventional nucleic acid synthesis techniques. For example, primers are synthesized on an automated DNA synthesizer (e.g., Applied Biosystems, Inc., Foster City, Calif.) using standard chemistries, such as phosphoramidite chemistry, and the like. Alternative chemistries, e.g., resulting in non-natural backbone groups, such as phosphorothioate, phosphoramidate, and the like, may also be employed provided that, for example, the resulting oligonucleotides are compatible with the polymerizing agent. The primers can also be ordered commercially from a variety of companies which specialize in custom nucleic acids such as Operon, Inc. (Alameda, Calif.). Primers comprising locked nucleic acids are purchased commercially (Proligo® LLC, Boulder, Colo.) or prepared as needed by methods known in the art.

The foregoing methods confer a significant advantage in single molecule reactions, in which one is tracking nucleotide incorporation into individual template/primer duplexes. Single molecule techniques provide the ability to observe discrete differences within and between individuals in terms of nucleotide sequence. Disruption of a hybrid impairs the ability to obtain full advantage from single molecule techniques because the loss of a hybrid represents the loss of significant information content relative to a bulk reaction in which there exist numerous copies of each hybrid pair. Methods of the invention maximize the ability to keep hybrid pairs intact and attached to substrate.

Primer Hybridization

Conditions for hybridizing primers to target nucleic acids are known in the art. The annealing reaction is performed under conditions which are stringent enough to ensure sequence specificity, yet sufficiently permissive to allow formation of stable hybrids at an acceptable rate. The temperature and length of time required for primer annealing depend upon several factors including the base composition, length and concentration of the primer, and the nature of the solvent used, e.g., the concentration of cosolvents such as DMSO (dimethylsulfoxide), formamide, or glycerol, and counterions such as magnesium. Typically, hybridization (annealing) is carried out at a temperature that is approximately 5 to 10° Celsius below the melting temperature of the primer/target nucleic acid duplex in the annealing solvent. Annealing temperatures may be modified based on the amount of locked nucleic acid included in the primer, based on manufacturer's recommendation and methods known in the art.

Primer Extension and Labeling

During primer extension, the primer/target nucleic acid duplex is exposed to a polymerase, and at least one nucleotide or nucleotide analog under conditions that allow for incorporation of the nucleotide into the primer. Polymerases useful in the invention include any polymerizing agent capable of catalyzing a template-dependant addition of a nucleotide to a primer, such as, Klenow, Vent ThermoSequenase®, 9° N™, Therminator, Taq, Tfl, Tth, Tli, Pfu, and others. According to one aspect of the invention, a thermophilic polymerase is used. In one embodiment, the invention provides for the primer/target nucleic acid duplex to be exposed to the polymerase and nucleotide at a temperature between about 30° and about 80° Celsius, or at least about 50°, 60°, or 70° Celsius.

Nucleotides useful in the invention include any nucleotide or nucleotide analog, whether naturally-occurring or synthetic. For example, preferred nucleotides are adenine, cytosine, guanine, uracil, or thymine bases; xanthine or hypoxanthine, 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, locked nucleic acids, oxetane-modified bases and any other structural moiety that can act substantially like a nucleotide or base, for example, by exhibiting base-complementarity with one or more bases that occur in DNA or RNA and/or being capable of base-complementary incorporation, and includes chain-terminating analogs.

Nucleotides particularly useful in the invention comprise detectable labels. Labeled nucleotides include any nucleotide that has been modified to include a label that is directly or indirectly detectable. Preferred labels include optically-detectable labels, including fluorescent labels or fluorophores, such as fluorescein, rhodamine, derivatized rhodamine dyes, such as TAMRA, phosphor, polymethadine dye, fluorescent phosphoramidite, Texas Red, green fluorescent protein, acridine, cyanine, cyanine 5 dye, cyanine 3 dye, 5-(2'-aminoethyl)-aminonaphthalene-1-sulfonic acid (EDANS), BODIPY, 120 ALEXA or a derivative or modification of any of the foregoing, and also include such labeling systems as hapten labeling. Accordingly, methods of the invention further provide for exposing the primer/target nucleic acid duplex to a digoxigenin, a fluorescein, an alkaline phosphatase or a peroxidase.

Other suitable fluorescent labels include, but are not limited to, 4-acetamido-4'-isothiocyanatostilbene-2,2'disulfonic acid; acridine and derivatives: acridine, acridine isothiocyanate; 4-amino-N-[3-vinylsulfonyl)phenyl]naphthalimide-3,5 disulfonate; N-(4-anilino-1-naphthyl)maleimide; anthranilamide; Brilliant Yellow; coumarin and derivatives: coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives; erythrosin B, erythrosin, isothiocyanate; ethidium; fluorescein derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine; tetramethyl rhodamine; tetramethyl rhodamine isothiocyanate (TRITC); riboflavin; rosolic acid; terbium chelate derivatives; Cy5.5; Cy7; IRD 700; IRD 800; La Jolta Blue; phthalo cyanine; and naphthalo cyanine.

In a preferred embodiment, after detection, the label is rendered undetectable by removing the label from the nucleotide or extended primer, neutralizing the label, or masking the label. In certain embodiments, methods according to the invention provide for neutralizing a label by photobleaching. This is accomplished by focusing a laser with a short laser pulse, for example, for a short duration of time with increasing laser intensity. In other embodiments, a label is photocleaved. For example, a light-sensitive label bound to a nucleotide is photocleaved by focusing a particular wavelength of light on the label. Generally, it may be preferable to use lasers having differing wavelengths for exciting and photocleaving. Labels also can be chemically cleaved. Labels may be removed from a substrate using reagents, such as NaOH or other appropriate buffer reagent.

Further, the primer or the target nucleic acid can also include a detectable label. When the labeled primer and/or target nucleic acid are attached to the substrate, the label facilitates locating the bound molecule through imaging. The primer or target nucleic acid can be labeled with a fluorescent labeling moiety (e.g., Cy3 or Cy5), or any other means used to label nucleotides. The detectable label used to label the primer or target nucleic acid can be different from the label used on the nucleotides or nucleotide analogs in the subsequent extension reactions. Additionally, once the molecule has been localized, it may be desirable to render the label undetectable prior to the nucleotide incorporation detection steps by methods such as washing or photobleaching.

A nucleotide analog according to the invention can be modified to remove, cap or modify the 3' hydroxyl group. As such, in certain embodiments, methods of the invention can include, for example, the step of removing the 3' hydroxyl group from the incorporated nucleotide or nucleotide analog. By removing the 3' hydroxyl group from the incorporated nucleotide in the primer, further extension is halted or impeded. In certain embodiments, the modified nucleotide can be engineered so that the 3' hydroxyl group can be removed and/or added by chemical methods. Alternatively, a nucleotide analog can be modified to include a moiety that is sufficiently large to prevent or sterically hinder further chain elongation by interfering with the polymerase, thereby halting incorporation of additional nucleotides or nucleotide analogs. Subsequent removal of the moiety, or at least the steric-hindering portion of the moiety, can concomitantly reverse chain termination and allow chain elongation to proceed. In some embodiments, the moiety also can be a label. As such, in those embodiments, chemically cleaving or photocleaving the blocking moiety may also chemically-bleach or photobleach the label, respectively.

Detection of Incorporated Nucleotides

Incorporation of a nucleotide or a nucleotide analog and their locations on the surface of a substrate can be detected with single molecule sensitivity according to the invention. In some aspects of the invention, single molecule resolution is achieved by anchoring a target nucleic acid at a low concentration to a substrate, and then imaging nucleotide incorporation with for example, with total internal reflection fluorescence microscopy.

A number of detection methods are available for use in single molecule analysis. Methods for visualizing single molecules within nucleic acids labeled with an intercalating dye include, for example, fluorescence microscopy. For example, the fluorescent spectrum and lifetime of a single molecule excited-state can be measured. Standard detectors such as a photomultiplier tube or avalanche photodiode can be used. Full field imaging with a two-stage image intensified COD camera also can be used. Additionally, low noise cooled CCD can also be used to detect single fluorescent molecules.

The detection system for the signal may depend upon the labeling moiety used, which can be defined by the chemistry available. For optical signals, a combination of an optical fiber or CCD can be used in the detection step. In the embodiments where the substrate is itself transparent to the radiation used, it is possible to have an incident light beam pass through the substrate with the detector located opposite the substrate from the primer. For electromagnetic labels, various forms of spectroscopy systems can be used. Various physical orientations for the detection system are available and known in the art.

A number of approaches can be used to detect incorporation of fluorescently-labeled nucleotides into a single molecule. Optical systems include near-field scanning microscopy, far-field confocal microscopy, wide-field epi-illumination, light scattering, dark field microscopy, photoconversion, single and/or multiphoton excitation, spectral wavelength discrimination, fluorophore identification, evanescent wave illumination, and total internal reflection fluorescence (TIRF) microscopy. In general, methods involve detection of laser-activated fluorescence using a microscope equipped with a camera, sometimes referred to as high-efficiency photon detection system. Suitable photon detection systems include, but are not limited to, photodiodes and intensified CCD cameras. For example, as illustrated in FIG. 2, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

Certain embodiments of the invention are described in the following examples, which are not meant to be limiting.

II. EXAMPLES

Example 1

Dual Biotinylation

General methods of the invention were demonstrated using biotin/avidin binding pairs. When a biotin-streptavidin linkage is used to anchor a primer and a target nucleic acid to a substrate, the primer and target nucleic acid are biotinylated, while the surface of the substrate is coated with streptavidin. Because streptavidin is a tetramer, it is possible that both template and primer will bind to the same surface streptavidin. However, the dual biotin labels may bind to adjacent streptavidin molecules as well.

Two experiments were done to determine the binding stability of the dual biotin constructs. A first experiment was conducted in order to determine the stability of dual biotin duplex on a polyelectrolyte multilayer (PEM) surface. This experiment was done using covalent streptavidin attachment to a PEM surface. The PEM surfaces were prepared as follows. Polyethyleneimine (PEI) and pollyallylamine (PAA, Sigma, St. Louis, Mo.) were dissolved separately by stirring in MilliQ water and the pH was adjusted to 8.0 with dilute HCl. The solutions were filtered using a 0.22µ filter flask and stored at 4° C. Clean glass slides were then alternatively immersed for 10 minutes in the PEI and PAA solutions four times each with an 8 minute rinse using MilliQ water between each immersion. After the last rinse, the slides were kept immersed in water. The slides were then transferred to MES buffer (2-[N-morpholino] ethanesulfonic acid), pH 5.5 for EDC-induced crosslinking of the PEM. A 10 mM solution of 1-[3-(dimethylamino)propyl]-3-ethylcarbodiimide hydrochloride (EDC) was prepared in MES buffer, filtered and added to the solution containing the PEM-coated slides for 1 hour at room temperature. Slides were then rinsed in MES buffer and stored.

Next, the PEM surfaces were amine-derivatized by treatment with 10 mM NHS and 10 mM EDC in 0.1 M MES buffer, pH 6.0, OSM NaCl (coupling buffer) for 15 minutes. The surfaces were then rinsed twice in the coupling buffer and incubated for 1 hour in 0.1 mg/ml Streptavidin Plus (SA-20, Prozyme) in the coupling buffer. The resulting streptavidinated surfaces were rinsed in a 200 µl solution of dual-biotin duplex in which the primer had the sequence: 5'-Biotin-TEG-AA AAA CCC CTT ATG CAC TTA TCC TTT ACT (SEQ ID NO: 1) and the template had the sequence: 5'-TCA GCT GCG TCA GCT AGC GAC AGT AAAGGATAAGTGCATAAGGGGTTTTT-TEG-Biotin (SEQ ID NO: 2; primer binding region bolded and underlined). At its 3' end, the terminal thymidine was labeled with cyanine-5 dye and the adenine two positions 5' of the terminus was labeled with a cyanine-3 dye. Surfaces were soaked for 5 minutes and then rinsed once in 20 mM Tris, pH 8.0, 50 mM NaCl, 0.01% Triton (Rinse Buffer). The surfaces were then rinsed 5 times in 3×SSC-0.1% Triton, with a 10 minute soak in the last rinse. Finally, the surfaces were rinsed in two changes of the Rinse Buffer. The resulting surface had dual-biotin primer/target nucleic acid duplex bound to streptavidin. A second set of slides was rinsed with the dual biotin duplexes as described above, but was also challenged with 100 nM unlabeled biotin. All slides were imaged over a 1000 µ$^2$ area and analyzed in ImagePro (Media Cybernetics, San Diego) using a dark image background subtraction algorithm.

Visualization of surface-bound duplexes was accomplished using fluorescence resonance energy transfer (FRET), with the cyanine-5 labeled thymidine as the donor and the cyanine-3 labeled adenine as the acceptor. Slides were placed on a Nikon Eclipse TE-2000 inverted microscope with a total internal reflection objective. The dual-biotin duplex slides showed 309.7 counts/pixel and the biotin-challenged slides showed 10.1 counts/pixel. These results indicate that the dual-biotin duplexes were binding to streptavidin on the PEM in a specific manner, as the cold biotin was able to compete away duplex binding.

Figure 5:
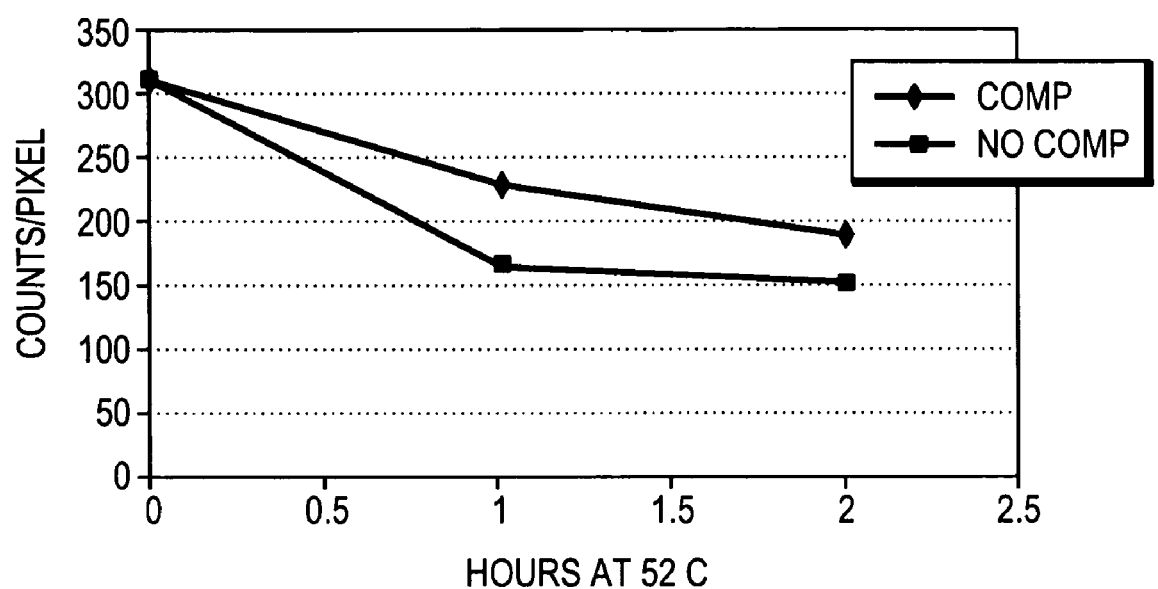
FIG. 5 shows the relative stability of dual biotin duplex on a streptavidinated PEM.

In a separate experiment, the dual biotin duplexes referred to above were first bound to a streptavidinated PEM surface as described above. The surface was then exposed to 100 nM unlabeled biotin at 52° C. for 10 minutes. As a control, streptavidinated PEMs were incubated in parallel and then rinsed with dual-biotin duplex. All slides then were washed, imaged, and analyzed as described above. The data are shown in FIG. 5. The results indicate that the dual-biotin duplexes on a streptavidinated PEM surface are surface-stable.

Another experiment shows the stability of dual-biotin duplexes in single molecule sequencing. For this experiment, streptavidinated slides are prepared on a PEM as described above. The slides then are biotinylated. Fresh biotin-long chain polyethyloxide-amine (Biotin-LC-PEO, Pierce) is prepared in MES buffer (50 mg Biotin in 2.5 ml MES). A 5 ml aliquot of the EDC solution described above is combined with 5 ml of the Biotin-LC-PEO solution and diluted in MES buffer to a total volume of 96 ml by adding 86 ml of MES buffer to a 2.5 mM final EDC-biotin concentration. The PEM-coated slides are then immersed in that solution in a 100 ml beaker and incubated for 60 minutes at room temperature. The slides are then rinsed in MES buffer with gentle agitation for 10 seconds. Immersion and rinsing are repeated four times in clean 100 ml volumes. Slides are then incubated in the final bath for 10 minutes. The resulting biotin-coated slides are stored in Tris-NaCl buffer prior to streptavidination.

Streptavidin-Plus (SA20, Prozyme) is dissolved in a solution of 10 mM NaCl buffer at 0.14 mg/ml and stirred 10 minutes at room temperature to thoroughly dissolve flakes. The resulting solution is filtered with a 0.22µ filter. Biotinylated slides described above are placed in this solution in a 100 ml beaker with a stir bar and stirred for 15 minutes at room temperature. The slides are then rinsed in 100 ml Tris-NaCl buffer with gentle agitation for 10 seconds. The rinse process is repeated 5 times in clean 100 ml volumes of 3×SSC-0.1% Triton, incubating in the final bath for 10 minutes. Finally, the slides are transferred to a fresh bath of Tris-NaCl and agitated for 10 seconds. Slides arestored in Tris-NaCl buffer at 4° C. prior to use.

3' bioinylated target nucleic acid templates: 5'-TCA GCT GCG TCA GCT AGC GAC AGT AAA GGA TAA GTG CAT AAG GGG TTT TT-TEG-Biotin (SEQ ID NO: 2), are obtained from Integrated DNA Technologies (Coral, IA). 5' biotinylated primers: 5'-Biotin-TEG-AA AAA CCC CTT ATG CAC TTA TCC TTT ACT (SEQ ID NO: 1), comprising a cyanine-5 dye were hybridized to the templates and exposed to the streptavidinated surfaces described above at a concentration of 10 pM. After incubation for 10 minutes, the surfaces are washed with MES buffer and the surface was imaged using a Nikon TE-2000U upright microscope equipped with a total internal reflection objective (Nikon). The location of label represented the location of bound hybrid and the positions of label are noted. Positional detection can also be accomplished using unlabeled template/primer and adding labeled first base. To determine the stability of bound duplexes, nucleotide additions are accomplished using the Klenow fragment (exo-) polymerase (New England Biolabs) at 10 mM in Ecopol reaction buffer and a series of cyanine-labeled nucleotide triphosphates. To reduce bleaching of the fluorescent dyes, an oxygen scavenging system is used (glucose (0.36%), glucose oxidase (8 U/ml), catalase (423 U/ml), Trolox (5 mM), Gallate (5 mM), DABCO (10 mM), and 2,4,6-octatrienoic acid).

The positions of cyanine-5-labeled primer are recorded and bleached. dUTP-Cy3 in polymerase is added to the slides. If dUTP is incorporated into the primer, fluorescence resonance energy transfer (FRET) from the cyanine-5 on the primer will caus the cyanine-3 dye to emit and the location of the emission is detected. The cyanine-3 dye is kept unbleached and subsequent additions are with cyanine-5-labeled dNTPs, using FRET with cyanine-3 as the donor for detection of incorporation. The results show that dual-biotin duplex is a stable template for template-dependent sequencing.

The skilled artisan understands that there are numerous other embodiments of the invention in terms of surfaces, binding partners and the like that can be manipulated in order to achieve the stability results shown above.

Example 2

Locked Nucleic Acid

A primer is designed to be complementary to a known primer attachment site of the target nucleic acid, and locked nucleic acid bases are substituted for certain nucleotides within the selected primer sequence. As many locked nucleic acid bases are selected as desired depending on the temperature and length of primer, up to a primer comprising 100% locked nucleic acids. The more locked nucleic acid substitutions into the primer, the greater the melting point of the primer/target nucleic acid duplex relative a primer of the same length lacking locked nucleic acid residues.

FIG. 3 shows three primers synthesized with locked nucleic acids. DXS17, 7G7A, and 377 primers were synthesized as complementary strands to known regions of a template, each primer incorporating nine locked nucleic acids. When these primers are annealed to their respective templates, hybridization may be carried out at temperatures between about 80° C. to about 90° C.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

I claim:

1. A method for stabilizing a nucleic acid duplex on a surface, the method comprising the steps of:
   contacting a surface with a nucleic acid duplex comprising a first and a second nucleic acid member, wherein each nucleic acid member comprises a binding pair member and at least one of said nucleic acid members comprises a binding pair member at its 3' terminus, wherein the surface comprises a binding partner for each of said binding pair members, and wherein said binding pair is a carbohydrate/lectin pair or an antigen/antibody pair,
   thereby to stabilize said duplex on said surface.

2. The method of claim 1, wherein each of said binding pair members is the same molecular species.

3. The method of claim 1, wherein each said member of said binding pair is a different molecular species.

4. The method of claim 1, wherein said binding pair is selected from the group consisting or biotin/avidin, biotin/streptavidin, digoxigenin/anti-digoxigenin, and dinitrophenol/anti-dinitrophenol.

5. The method of claim 1, wherein said nucleic acid duplex is a template/primer duplex.

6. The method of claim 1, wherein each of said binding pair members is located at the 5' terminus of said template and the 3' terminus of said primer.

7. The method of claim 1, wherein one of said binding pair members is located at the 5' terminus of said primer.

8. The method of claim 5, further comprising the steps of contacting a surface-bound nucleic acid duplex to a nucleotide base and a polymerase under conditions sufficient for said nucleotide base to be incorporated into said primer if said nucleotide base is complementary to a corresponding base in said template.

9. The method of claim 8, further comprising the step of compiling a nucleic acid sequence of said template by detecting sequential incorporations of nucleotides into said primer.

10. The method of claim 5, wherein said primer comprises a locked nucleic acid base.

11. The method of claim 5, wherein said primer comprises a peptide nucleic acid base.

12. A method for performing a nucleic acid sequencing reaction, the method comprising:
   contacting a mixture comprising a nucleic acid template, a polymerase, and a primer, wherein said primer comprises a locked nucleic acid, with a nucleotide under conditions wherein said nucleotide is capable of incorporation into said primer, wherein said nucleic acid template and said primer each comprises a binding pair member, and wherein said template and said primer form a stabilized nucleic acid duplex on a surface, the surface comprising a binding partner for each said binding pair member, and wherein said binding pair is a carbohydrate/lectin pair or an antigen/antibody pair, thereby performing a nucleic acid sequencing reaction.

13. The method of claim 1, wherein a plurality of said nucleic acid duplexes is attached to a substrate such that each of said nucleic acid duplexes is individually optically resolvable.

14. The method of claim 12, further comprising detecting ordered template-dependent nucleotide incorporation into the primer and compiling a sequence of the template based upon the order or incorporated nucleotides.

* * * * *